（12） United States Patent
Shaolian et al.

(10) Patent No.: US 8,034,100 B2
(45) Date of Patent: Oct. 11, 2011

(54) GRAFT DEPLOYMENT SYSTEM

(75) Inventors: Samuel M. Shaolian, Newport Beach, CA (US); Gilbert Madrid, Laguna Niguel, CA (US); To Van Pham, Trabuco Canyon, CA (US); Trinh Van Pham, Santa Ana, CA (US)

(73) Assignee: Endologix, Inc., Irvine, CA (US)

( * ) Notice: Subject to any disclaimer, the term of this patent is extended or adjusted under 35 U.S.C. 154(b) by 968 days.

(21) Appl. No.: 10/722,367

(22) Filed: Nov. 25, 2003

(65) Prior Publication Data

US 2004/0167618 A1 Aug. 26, 2004

Related U.S. Application Data

(60) Continuation of application No. 09/795,993, filed on Feb. 28, 2001, now Pat. No. 6,663,665, which is a division of application No. 09/266,661, filed on Mar. 11, 1999, now Pat. No. 6,261,316.

(60) Provisional application No. 60/429,666, filed on Nov. 26, 2002.

(51) Int. Cl.
*A61F 2/84* (2006.01)
(52) U.S. Cl. ..................... 623/1.23; 623/1.11
(58) Field of Classification Search .............. 623/1.11, 623/1.12, 1.35, 1.23; 604/164.05; 606/108
See application file for complete search history.

(56) References Cited

U.S. PATENT DOCUMENTS

| | | | |
|---|---|---|---|
| 2,127,903 A | 8/1938 | Bowen |
| 2,437,542 A | 5/1944 | Krippendorf |
| 2,845,959 A | 8/1958 | Sidebotham |
| 2,990,605 A | 7/1961 | Demsyk |
| 3,029,819 A | 4/1962 | Starks |
| 3,096,560 A | 7/1963 | Liebig |
| 3,805,301 A | 4/1974 | Liebig |
| 4,497,074 A | 2/1985 | Rey et al. |
| 4,501,263 A | 2/1985 | Harbuck |
| 4,503,568 A | 3/1985 | Madras |

(Continued)

FOREIGN PATENT DOCUMENTS

CA 2133530 1/1999

(Continued)

OTHER PUBLICATIONS

Patent Cooperation Treaty (PCT) International Search Report, International Application No. PCT/US2007/078565, Filed on Sep. 14, 2007, in 7 pages.

(Continued)

*Primary Examiner* — Ryan Severson
(74) *Attorney, Agent, or Firm* — Knobbe, Martens, Olson & Bear LLP

(57) ABSTRACT

A graft deployment system, comprises an elongate, flexible catheter body, having a proximal end and a distal end and comprising an outer sheath and an inner core that is axially moveable with respect to the outer sheath. A main vessel graft restraint comprising a first peelable cover for restrains a main vessel portion of a graft. In a bifurcated graft, a first branch vessel graft restraint restrains a first branch vessel portion of the graft. A second branch vessel graft restraint restrains a second branch vessel portion of the graft. The first peelable cover is coupled to a main branch release element and wherein each of the main vessel graft restraint, first branch vessel graft restraint, and the second branch vessel graft restraint are positioned within the catheter body in a graft loaded condition.

31 Claims, 28 Drawing Sheets

U.S. PATENT DOCUMENTS

| | | |
|---|---|---|
| 4,580,568 A | 4/1986 | Gianturco |
| 4,592,754 A | 6/1986 | Gupte et al. |
| 4,617,932 A | 10/1986 | Kornberg |
| 4,756,307 A | 7/1988 | Crownshield |
| 4,800,882 A | 1/1989 | Gianturco |
| 4,816,028 A | 3/1989 | Kapadia et al. |
| 4,840,940 A | 6/1989 | Sottiurai |
| 4,856,516 A | 8/1989 | Hillstead |
| 4,878,906 A | 11/1989 | Lindemann et al. |
| 4,907,336 A | 3/1990 | Gianturco |
| 4,922,905 A | 5/1990 | Strecker |
| 4,981,478 A | 1/1991 | Evard et al. |
| 4,981,947 A | 1/1991 | Tomagou et al. |
| 4,994,071 A | 2/1991 | Macgregor |
| 5,019,090 A | 5/1991 | Pinchuk |
| 5,026,377 A * | 6/1991 | Burton et al. ............... 606/108 |
| 5,035,706 A | 7/1991 | Giantureo et al. |
| 5,064,435 A | 11/1991 | Porter |
| 5,078,726 A | 1/1992 | Kreamer |
| 5,104,399 A | 4/1992 | Lazarus |
| 5,108,424 A | 4/1992 | Hoffman, Jr. et al. |
| 5,116,349 A | 5/1992 | Aranyi |
| 5,123,917 A | 6/1992 | Lee |
| 5,133,732 A | 7/1992 | Wiktor |
| 5,135,535 A | 8/1992 | Kramer |
| 5,135,536 A | 8/1992 | Hillstead |
| 5,156,619 A | 10/1992 | Ehrenfeld |
| 5,158,545 A * | 10/1992 | Trudell et al. ............... 604/509 |
| 5,178,634 A | 1/1993 | Martinez |
| 5,197,976 A | 3/1993 | Herweck et al. |
| 5,201,757 A | 4/1993 | Heyn et al. |
| 5,211,658 A | 5/1993 | Clouse |
| 5,246,452 A * | 9/1993 | Sinnott ............... 623/1.23 |
| 5,256,141 A | 10/1993 | Gencheff et al. |
| 5,275,622 A | 1/1994 | Lazarus et al. |
| 5,282,824 A | 2/1994 | Gianturco |
| 5,282,860 A | 2/1994 | Matsuno et al. |
| 5,304,200 A | 4/1994 | Spaulding |
| 5,314,444 A | 5/1994 | Gianturco |
| 5,314,472 A | 5/1994 | Fontaine |
| 5,316,023 A | 5/1994 | Palmaz et al. |
| 5,320,602 A | 6/1994 | Karpeil |
| 5,330,500 A | 7/1994 | Song |
| 5,342,387 A | 8/1994 | Summers |
| 5,354,308 A | 10/1994 | Simon et al. |
| 5,360,443 A | 11/1994 | Barone et al. |
| 5,366,504 A | 11/1994 | Andersen et al. |
| 5,370,683 A | 12/1994 | Fontaine |
| 5,387,235 A | 2/1995 | Chuter |
| 5,397,355 A | 3/1995 | Marin et al. |
| 5,403,341 A | 4/1995 | Solar |
| 5,405,377 A | 4/1995 | Cragg |
| 5,405,378 A | 4/1995 | Strecker |
| 5,415,664 A | 5/1995 | Pinchuk |
| 5,423,886 A | 6/1995 | Arru et al. |
| 5,425,765 A | 6/1995 | Tiefenbrun et al. |
| 5,443,477 A | 8/1995 | Marin et al. |
| 5,443,498 A | 8/1995 | Fontaine |
| 5,443,500 A | 8/1995 | Sigwart |
| 5,453,090 A | 9/1995 | Martinez et al. |
| 5,456,713 A | 10/1995 | Chuter |
| 5,458,615 A | 10/1995 | Klemm et al. |
| 5,462,530 A | 10/1995 | Jang |
| 5,464,449 A | 11/1995 | Ryan et al. |
| 5,464,450 A | 11/1995 | Buscemi et al. |
| 5,484,444 A | 1/1996 | Braunschweiler et al. |
| 5,489,295 A | 2/1996 | Piplani et al. |
| 5,496,365 A | 3/1996 | Sgro |
| 5,507,767 A | 4/1996 | Maeda et al. |
| 5,507,768 A | 4/1996 | Lau et al. |
| 5,507,769 A | 4/1996 | Marin et al. |
| 5,507,771 A | 4/1996 | Gianturco |
| 5,522,880 A | 6/1996 | Barone et al. |
| 5,522,881 A | 6/1996 | Lentz |
| 5,522,883 A | 6/1996 | Slater et al. |
| 5,545,211 A | 8/1996 | An et al. |
| 5,549,635 A | 8/1996 | Solar |
| 5,554,118 A | 9/1996 | Jang |
| 5,554,181 A | 9/1996 | Das |
| 5,562,697 A | 10/1996 | Christiansen |
| 5,562,726 A | 10/1996 | Chuter |
| 5,562,728 A | 10/1996 | Lazarus et al. |
| 5,571,169 A | 11/1996 | Plaia et al. |
| 5,571,172 A | 11/1996 | Chin |
| 5,571,173 A | 11/1996 | Parodi |
| 5,575,816 A | 11/1996 | Rudnick et al. |
| 5,575,818 A | 11/1996 | Pinchuk |
| 5,578,071 A | 11/1996 | Parodi |
| 5,578,072 A | 11/1996 | Barone et al. |
| 5,591,197 A | 1/1997 | Orth et al. |
| 5,591,198 A | 1/1997 | Boyle et al. |
| 5,591,226 A * | 1/1997 | Trerotola et al. ............ 623/1.12 |
| 5,591,228 A * | 1/1997 | Edoga ............... 128/898 |
| 5,591,229 A | 1/1997 | Parodi |
| 5,591,230 A | 1/1997 | Horn et al. |
| 5,593,417 A | 1/1997 | Rhodes |
| 5,599,305 A | 2/1997 | Hermann et al. |
| 5,604,435 A | 2/1997 | Foo et al. |
| 5,607,445 A | 3/1997 | Summers |
| 5,609,625 A | 3/1997 | Piplani et al. |
| 5,609,627 A | 3/1997 | Goicoechea et al. |
| 5,609,628 A | 3/1997 | Keranen |
| 5,628,783 A | 5/1997 | Quiachon et al. |
| 5,628,786 A | 5/1997 | Banas et al. |
| 5,628,788 A | 5/1997 | Pinchuk |
| 5,630,829 A | 5/1997 | Lauterjung |
| 5,630,830 A | 5/1997 | Verbeek |
| 5,632,763 A | 5/1997 | Glastra |
| 5,632,772 A | 5/1997 | Alcime et al. |
| 5,639,278 A | 6/1997 | Dereume et al. |
| 5,641,373 A | 6/1997 | Shannon et al. |
| 5,643,171 A | 7/1997 | Bradshaw et al. |
| 5,643,278 A | 7/1997 | Wijay |
| 5,643,339 A | 7/1997 | Kavteladze et al. |
| 5,643,748 A | 7/1997 | Snodgrass et al. |
| 5,647,857 A * | 7/1997 | Anderson et al. ............ 604/264 |
| 5,649,952 A | 7/1997 | Lam |
| 5,651,174 A | 7/1997 | Schwartz et al. |
| 5,653,727 A | 8/1997 | Wiktor |
| 5,653,743 A | 8/1997 | Martin |
| 5,653,746 A | 8/1997 | Schmitt |
| 5,653,747 A | 8/1997 | Dereume |
| 5,662,580 A | 9/1997 | Bradshaw et al. |
| 5,662,614 A | 9/1997 | Edoga |
| 5,662,700 A | 9/1997 | Lazarus |
| 5,662,701 A | 9/1997 | Plaia et al. |
| 5,662,702 A | 9/1997 | Keranen |
| 5,662,703 A | 9/1997 | Yurek et al. |
| 5,665,115 A | 9/1997 | Cragg |
| 5,665,117 A | 9/1997 | Rhodes |
| 5,669,924 A | 9/1997 | Shaknovich |
| 5,674,241 A | 10/1997 | Bley et al. |
| 5,674,276 A | 10/1997 | Andersen et al. |
| 5,676,685 A | 10/1997 | Razaivi |
| 5,676,696 A | 10/1997 | Marcade |
| 5,676,697 A | 10/1997 | McDonald |
| 5,679,400 A | 10/1997 | Tuch |
| 5,681,345 A | 10/1997 | Tuteneuer |
| 5,681,346 A | 10/1997 | Orth et al. |
| 5,683,448 A | 11/1997 | Cragg |
| 5,683,449 A | 11/1997 | Marcade |
| 5,683,450 A | 11/1997 | Goicoechea et al. |
| 5,683,451 A | 11/1997 | Lenker et al. |
| 5,683,452 A | 11/1997 | Barone et al. |
| 5,683,453 A | 11/1997 | Palmaz |
| 5,690,642 A | 11/1997 | Osborne et al. |
| 5,690,643 A | 11/1997 | Wijay |
| 5,690,644 A | 11/1997 | Yurek et al. |
| 5,693,066 A | 12/1997 | Rupp et al. |
| 5,693,084 A | 12/1997 | Chuter |
| 5,693,086 A | 12/1997 | Goicoechea et al. |
| 5,693,087 A | 12/1997 | Parodi |
| 5,693,088 A | 12/1997 | Lazarus |
| 5,695,516 A | 12/1997 | Fischell et al. |
| 5,695,517 A | 12/1997 | Marin et al. |
| 5,697,948 A | 12/1997 | Marin et al. |
| 5,709,703 A | 1/1998 | Lukic et al. |

| Patent | Date | Inventor |
|---|---|---|
| 5,713,917 A | 2/1998 | Leonhardt et al. |
| 5,716,365 A | 2/1998 | Goicoechea et al. |
| 5,716,393 A | 2/1998 | Lindenberg et al. |
| 5,718,724 A | 2/1998 | Goicoechea et al. |
| 5,718,973 A | 2/1998 | Lewis et al. |
| 5,720,735 A * | 2/1998 | Dorros ............... 604/284 |
| 5,720,776 A | 2/1998 | Chuter et al. |
| 5,723,004 A | 3/1998 | Dereume et al. |
| 5,733,267 A * | 3/1998 | Del Toro ............... 623/1.11 |
| 5,733,325 A | 3/1998 | Robinson et al. |
| 5,746,766 A | 5/1998 | Edoga |
| 5,746,776 A | 5/1998 | Smith et al. |
| 5,749,880 A | 5/1998 | Banas et al. |
| 5,755,770 A | 5/1998 | Ravenscroft |
| 5,755,771 A | 5/1998 | Penn et al. |
| 5,755,777 A | 5/1998 | Chuter |
| 5,766,203 A | 6/1998 | Imran et al. |
| 5,769,885 A * | 6/1998 | Quiachon et al. ............ 128/898 |
| 5,769,887 A | 6/1998 | Brown et al. |
| 5,782,855 A | 7/1998 | Lau et al. |
| 5,782,909 A | 7/1998 | Quiachon et al. |
| 5,800,456 A | 9/1998 | Maeda et al. |
| 5,800,508 A | 9/1998 | Goicoechea et al. |
| 5,800,526 A | 9/1998 | Anderson et al. |
| 5,800,540 A | 9/1998 | Chin |
| 5,810,836 A | 9/1998 | Hussein et al. |
| 5,817,100 A | 10/1998 | Igaki |
| 5,824,037 A | 10/1998 | Fogarty et al. |
| 5,824,039 A | 10/1998 | Piplani et al. |
| 5,824,040 A | 10/1998 | Cox et al. |
| 5,824,053 A | 10/1998 | Khosravi et al. |
| 5,843,160 A | 12/1998 | Rhodes |
| 5,843,162 A | 12/1998 | Inoue |
| 5,843,164 A | 12/1998 | Frantzen et al. |
| 5,843,167 A | 12/1998 | Dwyer et al. |
| 5,851,228 A | 12/1998 | Pinheiro |
| 5,855,599 A | 1/1999 | Wan |
| 5,860,998 A | 1/1999 | Robinson et al. |
| 5,865,844 A | 2/1999 | Plaia et al. |
| 5,867,432 A | 2/1999 | Toda |
| 5,868,783 A | 2/1999 | Tower |
| 5,871,536 A | 2/1999 | Lazarus |
| 5,873,906 A | 2/1999 | Lau et al. |
| 5,879,321 A | 3/1999 | Hill |
| 5,879,366 A | 3/1999 | Shau et al. |
| 5,891,193 A | 4/1999 | Robinson et al. |
| 5,893,868 A | 4/1999 | Hanson et al. |
| 5,893,887 A | 4/1999 | Jayaraman |
| 5,902,334 A | 5/1999 | Dwyer et al. |
| 5,906,640 A | 5/1999 | Penn et al. |
| 5,906,641 A | 5/1999 | Thompson et al. |
| 5,916,263 A | 6/1999 | Goicoechea et al. |
| 5,919,225 A | 7/1999 | Lau et al. |
| 5,925,075 A | 7/1999 | Myers et al. |
| 5,928,279 A | 7/1999 | Shannon et al. |
| 5,935,161 A | 8/1999 | Robinson et al. |
| 5,938,696 A | 8/1999 | Goicoechea et al. |
| 5,948,018 A | 9/1999 | Dereume et al. |
| 5,957,973 A | 9/1999 | Quiachon et al. |
| 5,961,546 A | 10/1999 | Robinson et al. |
| 5,961,548 A | 10/1999 | Shmulewitz |
| 6,001,125 A | 12/1999 | Golds et al. |
| 6,004,347 A | 12/1999 | McNamara et al. |
| 6,004,348 A | 12/1999 | Banas et al. |
| 6,017,363 A | 1/2000 | Hojeibane |
| 6,019,785 A | 2/2000 | Strecker |
| 6,027,508 A | 2/2000 | Ren et al. |
| 6,027,779 A | 2/2000 | Campbell et al. |
| 6,027,811 A | 2/2000 | Campbell et al. |
| 6,030,415 A | 2/2000 | Chuter |
| 6,039,749 A | 3/2000 | Marin et al. |
| 6,039,755 A | 3/2000 | Edwin et al. |
| 6,039,758 A | 3/2000 | Quiachon et al. |
| 6,045,557 A | 4/2000 | White et al. |
| 6,051,020 A | 4/2000 | Goicoechea et al. |
| 6,053,940 A | 4/2000 | Wijay |
| 6,056,722 A | 5/2000 | Jayaraman |
| 6,059,813 A | 5/2000 | Vrba et al. |
| 6,063,092 A | 5/2000 | Shin |
| 6,063,113 A | 5/2000 | Kavteladze et al. |
| 6,070,589 A | 6/2000 | Keith et al. |
| 6,074,398 A | 6/2000 | Leschinsky |
| 6,077,296 A | 6/2000 | Shokooji et al. |
| 6,077,297 A | 6/2000 | Robinson et al. |
| 6,086,611 A | 7/2000 | Duffy et al. |
| 6,090,128 A | 7/2000 | Douglas |
| 6,090,135 A | 7/2000 | Plaia et al. |
| 6,093,194 A | 7/2000 | Mikus et al. |
| 6,093,203 A | 7/2000 | Uflacker |
| 6,096,027 A | 8/2000 | Layne |
| 6,106,548 A | 8/2000 | Reubin et al. |
| 6,113,607 A | 9/2000 | Lau et al. |
| 6,117,167 A | 9/2000 | Goicoechea et al. |
| 6,123,722 A | 9/2000 | Fogarty et al. |
| 6,123,723 A | 9/2000 | Konya et al. |
| 6,126,685 A | 10/2000 | Lenker et al. |
| 6,129,756 A | 10/2000 | Kugler et al. |
| 6,143,016 A | 11/2000 | Bleam et al. |
| 6,146,389 A | 11/2000 | Geitz |
| 6,152,944 A | 11/2000 | Holman et al. |
| 6,162,237 A | 12/2000 | Chan |
| 6,165,214 A | 12/2000 | Lazarus |
| 6,168,610 B1 | 1/2001 | Marin et al. |
| 6,171,281 B1 | 1/2001 | Zhang |
| 6,183,481 B1 | 2/2001 | Lee et al. |
| 6,183,509 B1 | 2/2001 | Dibie |
| 6,187,036 B1 | 2/2001 | Shaolian et al. |
| 6,192,944 B1 | 2/2001 | Greenhalgh |
| 6,197,049 B1 | 3/2001 | Shaolian et al. |
| 6,203,735 B1 | 3/2001 | Edwin et al. |
| 6,214,038 B1 | 4/2001 | Piplani et al. |
| 6,221,081 B1 | 4/2001 | Mikus et al. |
| 6,221,102 B1 | 4/2001 | Baker et al. |
| 6,224,627 B1 | 5/2001 | Armstrong et al. |
| 6,231,563 B1 | 5/2001 | White et al. |
| 6,238,410 B1 | 5/2001 | Vrba et al. |
| 6,254,609 B1 | 7/2001 | Vrba et al. |
| 6,254,628 B1 | 7/2001 | Wallace et al. |
| 6,261,316 B1 * | 7/2001 | Shaolian et al. ............ 623/1.11 |
| 6,273,909 B1 | 8/2001 | Kugler et al. |
| 6,280,466 B1 | 8/2001 | Kugler et al. |
| 6,280,467 B1 | 8/2001 | Leonhardt |
| 6,283,991 B1 | 9/2001 | Cox et al. |
| 6,287,329 B1 | 9/2001 | Duerig et al. |
| 6,299,634 B1 | 10/2001 | Bergeron |
| 6,312,406 B1 | 11/2001 | Jayaraman |
| 6,331,184 B1 | 12/2001 | Abrams |
| 6,346,118 B1 | 2/2002 | Baker et al. |
| 6,348,066 B1 | 2/2002 | Pinchuk et al. |
| 6,350,278 B1 | 2/2002 | Lenker et al. |
| 6,352,553 B1 | 3/2002 | Van der Burg et al. |
| 6,352,561 B1 | 3/2002 | Leopold et al. |
| 6,355,060 B1 | 3/2002 | Lenker et al. |
| 6,361,557 B1 | 3/2002 | Gittings et al. |
| 6,361,559 B1 | 3/2002 | Houser et al. |
| 6,361,637 B2 | 3/2002 | Martin et al. |
| 6,380,457 B1 | 4/2002 | Yurek et al. |
| 6,395,017 B1 | 5/2002 | Dwyer et al. |
| 6,395,018 B1 | 5/2002 | Castaneda |
| 6,395,019 B2 | 5/2002 | Chobotov |
| 6,398,807 B1 | 6/2002 | Chouinard et al. |
| 6,409,750 B1 | 6/2002 | Hyodoh et al. |
| 6,409,757 B1 | 6/2002 | Trout, III et al. |
| 6,416,474 B1 | 7/2002 | Penner et al. |
| 6,416,529 B1 | 7/2002 | Holman et al. |
| 6,416,542 B1 | 7/2002 | Marcade et al. |
| 6,432,130 B1 | 8/2002 | Hanson |
| 6,432,131 B1 | 8/2002 | Ravenscroft |
| 6,432,134 B1 | 8/2002 | Anson et al. |
| 6,447,540 B1 | 9/2002 | Fontaine et al. |
| 6,464,721 B1 | 10/2002 | Marcade et al. |
| 6,475,166 B1 | 11/2002 | Escano |
| 6,475,170 B1 | 11/2002 | Doron et al. |
| 6,482,211 B1 | 11/2002 | Choi |
| 6,485,513 B1 | 11/2002 | Fan |
| 6,491,719 B1 | 12/2002 | Fogrty et al. |
| 6,500,202 B1 | 12/2002 | Shaolian et al. |
| 6,508,833 B2 | 1/2003 | Pavcnick et al. |

| | | |
|---|---|---|
| 6,508,835 B1 | 1/2003 | Shaolian et al. |
| 6,511,325 B1 | 1/2003 | Lalka et al. |
| 6,514,281 B1 | 2/2003 | Blaeser et al. |
| 6,514,282 B1 | 2/2003 | Inoue |
| 6,517,569 B2 | 2/2003 | Mikus et al. |
| 6,517,572 B2 | 2/2003 | Kugler et al. |
| 6,517,573 B1 | 2/2003 | Pollock et al. |
| 6,520,988 B1 | 2/2003 | Colombo et al. |
| 6,524,335 B1 | 2/2003 | Hartley et al. |
| 6,533,811 B1 | 3/2003 | Ryan et al. |
| 6,544,278 B1 | 4/2003 | Vrba et al. |
| 6,551,350 B1 | 4/2003 | Thornton et al. |
| 6,558,396 B1 | 5/2003 | Inoue |
| 6,562,063 B1 | 5/2003 | Euteneuer et al. |
| 6,565,596 B1 | 5/2003 | White et al. |
| 6,565,597 B1 | 5/2003 | Fearnot et al. |
| RE38,146 E | 6/2003 | Palmaz et al. |
| 6,572,645 B2 | 6/2003 | Leonhardt |
| 6,576,005 B1 | 6/2003 | Geitz |
| 6,576,009 B2 | 6/2003 | Ryan et al. |
| 6,582,460 B1 | 6/2003 | Cryer |
| 6,585,758 B1 | 7/2003 | Chouinard et al. |
| 6,592,548 B2 | 7/2003 | Jayaraman |
| 6,592,614 B2 | 7/2003 | Lenker et al. |
| 6,592,615 B1 | 7/2003 | Marcade et al. |
| 6,607,552 B1 | 8/2003 | Hanson |
| 6,613,073 B1 | 9/2003 | White et al. |
| 6,616,675 B1 | 9/2003 | Evard et al. |
| 6,652,579 B1 | 11/2003 | Cox et al. |
| 6,656,213 B1 | 12/2003 | Solem |
| 6,663,665 B2 | 12/2003 | Shaolian et al. |
| 6,669,718 B2 | 12/2003 | Besselink |
| 6,669,719 B2 | 12/2003 | Wallace et al. |
| 6,676,666 B2 | 1/2004 | Vrba et al. |
| 6,702,843 B1 | 3/2004 | Brown et al. |
| 6,733,523 B2 | 5/2004 | Shaolian et al. |
| 6,755,855 B2 | 6/2004 | Yurek et al. |
| 6,761,733 B2 | 7/2004 | Chobotov et al. |
| 6,767,359 B2 | 7/2004 | Weadock |
| 6,790,224 B2 | 9/2004 | Gerberding |
| 6,818,014 B2 | 11/2004 | Brown et al. |
| 6,821,292 B2 | 11/2004 | Pazienza et al. |
| 6,840,950 B2 | 1/2005 | Stanford et al. |
| 6,846,316 B2 | 1/2005 | Abrams |
| 6,858,038 B2 | 2/2005 | Heuser |
| 6,887,249 B1 | 5/2005 | Houser et al. |
| 6,887,251 B1 | 5/2005 | Suval |
| 6,899,727 B2 | 5/2005 | Armstrong et al. |
| 6,899,728 B1 | 5/2005 | Phillips et al. |
| 6,923,829 B2 | 8/2005 | Boyle et al. |
| 6,929,661 B2 | 8/2005 | Bolduc et al. |
| 6,932,837 B2 | 8/2005 | Amplatz et al. |
| 6,939,368 B2 | 9/2005 | Simso |
| 6,939,371 B2 | 9/2005 | Kugler et al. |
| 6,939,377 B2 | 9/2005 | Jayaraman et al. |
| 6,942,692 B2 | 9/2005 | Landau et al. |
| 6,942,693 B2 | 9/2005 | Chouinard et al. |
| 6,953,475 B2 | 10/2005 | Shaolian et al. |
| 6,955,679 B1 | 10/2005 | Hendricksen et al. |
| 6,960,217 B2 | 11/2005 | Bolduc |
| 6,981,982 B2 | 1/2006 | Armstrong et al. |
| 6,984,244 B2 | 1/2006 | Perez et al. |
| 6,991,639 B2 | 1/2006 | Holman et al. |
| 6,994,722 B2 | 2/2006 | DiCarlo |
| 7,004,926 B2 | 2/2006 | Navia et al. |
| 7,004,964 B2 | 2/2006 | Thompson et al. |
| 7,004,967 B2 | 2/2006 | Chouinard et al. |
| 7,014,653 B2 | 3/2006 | Ouriel et al. |
| 7,025,779 B2 | 4/2006 | Elliott |
| 7,029,496 B2 | 4/2006 | Rakos et al. |
| 7,074,236 B2 | 7/2006 | Rabkin et al. |
| 7,122,051 B1 | 10/2006 | Dallara et al. |
| 7,122,052 B2 | 10/2006 | Greenhalgh |
| 7,125,464 B2 | 10/2006 | Chobotov et al. |
| 7,144,422 B1 | 12/2006 | Rao |
| 7,160,318 B2 | 1/2007 | Greenberg et al. |
| 7,162,302 B2 | 1/2007 | Wang et al. |
| 7,163,715 B1 | 1/2007 | Kramer |
| 7,175,652 B2 | 2/2007 | Cook et al. |
| 7,175,657 B2 | 2/2007 | Khan et al. |
| 7,189,256 B2 | 3/2007 | Smith |
| 7,201,770 B2 | 4/2007 | Johnson et al. |
| 7,235,095 B2 | 6/2007 | Haverkost et al. |
| 7,244,444 B2 | 7/2007 | Bates |
| 7,261,733 B1 | 8/2007 | Brown et al. |
| 7,264,631 B2 | 9/2007 | DeCarlo |
| 7,264,632 B2 | 9/2007 | Wright et al. |
| 7,267,685 B2 | 9/2007 | Butaric et al. |
| 7,270,675 B2 | 9/2007 | Chun et al. |
| 7,285,130 B2 | 10/2007 | Austin |
| 7,314,483 B2 | 1/2008 | Landau et al. |
| 7,320,703 B2 | 1/2008 | DiMatteo et al. |
| 7,402,168 B2 | 7/2008 | Acosta et al. |
| 7,491,230 B2 | 2/2009 | Holman et al. |
| 7,520,895 B2 | 4/2009 | Douglas et al. |
| 7,553,324 B2 | 6/2009 | Andreas et al. |
| 7,572,289 B2 | 8/2009 | Sisken et al. |
| 7,637,932 B2 | 12/2009 | Bolduc et al. |
| 7,651,519 B2 | 1/2010 | Dittman |
| 7,674,284 B2 | 3/2010 | Melsheimer |
| 7,691,135 B2 | 4/2010 | Shaolian et al. |
| 7,722,657 B2 | 5/2010 | Hartley |
| 7,833,259 B2 | 11/2010 | Boatman |
| 2001/0001128 A1 | 5/2001 | Holman et al. |
| 2002/0029077 A1 | 3/2002 | Leopold et al. |
| 2002/0049412 A1 | 4/2002 | Madrid et al. |
| 2002/0123786 A1 | 9/2002 | Gittings et al. |
| 2003/0004560 A1 | 1/2003 | Chobotov et al. |
| 2003/0097169 A1 | 5/2003 | Brucker et al. |
| 2003/0149465 A1 | 8/2003 | Heidner et al. |
| 2003/0236565 A1 | 12/2003 | DiMatteo et al. |
| 2004/0010265 A1 | 1/2004 | Karpiel |
| 2004/0176832 A1 | 9/2004 | Hartley et al. |
| 2005/0033403 A1 | 2/2005 | Ward et al. |
| 2005/0038494 A1 | 2/2005 | Eidenschink |
| 2005/0049672 A1 | 3/2005 | Murphy |
| 2005/0058327 A1 | 3/2005 | Pieper |
| 2005/0059994 A1 | 3/2005 | Walak et al. |
| 2005/0060025 A1 | 3/2005 | Mackiewicz et al. |
| 2005/0085842 A1 | 4/2005 | Eversull et al. |
| 2005/0085845 A1 | 4/2005 | Hilaire et al. |
| 2005/0113693 A1 | 5/2005 | Smith et al. |
| 2005/0113905 A1 | 5/2005 | Greenberg et al. |
| 2005/0119731 A1 | 6/2005 | Brucker et al. |
| 2005/0121043 A1 | 6/2005 | Abrams |
| 2005/0121120 A1 | 6/2005 | Van Dijk et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0216043 A1 | 9/2005 | Blatter et al. |
| 2005/0228476 A1 | 10/2005 | Dimatteo et al. |
| 2005/0234542 A1 | 10/2005 | Melsheimer |
| 2005/0240153 A1 | 10/2005 | Opie |
| 2005/0240258 A1 | 10/2005 | Bolduc et al. |
| 2005/0240260 A1 | 10/2005 | Bolduc |
| 2005/0273150 A1 | 12/2005 | Howel et al. |
| 2005/0288772 A1 | 12/2005 | Douglas |
| 2006/0030924 A1 | 2/2006 | Van Der Leest et al. |
| 2006/0100686 A1 | 5/2006 | Bolduc et al. |
| 2006/0142838 A1 | 6/2006 | Molaei et al. |
| 2006/0217794 A1 | 9/2006 | Ruiz et al. |
| 2006/0233990 A1 | 10/2006 | Humphrey et al. |
| 2006/0233991 A1 | 10/2006 | Humphrey et al. |
| 2006/0287713 A1 | 12/2006 | Douglas et al. |
| 2007/0010867 A1 | 1/2007 | Carter et al. |
| 2007/0027522 A1 | 2/2007 | Chang et al. |
| 2007/0027526 A1 | 2/2007 | Demetriades et al. |
| 2007/0027531 A1 | 2/2007 | DeMatteo et al. |
| 2007/0112420 A1 | 5/2007 | LaDuca |
| 2007/0203571 A1 | 8/2007 | Kaplan et al. |
| 2007/0213805 A1 | 9/2007 | Schaeffer et al. |
| 2007/0244540 A1 | 10/2007 | Pryor |
| 2007/0260302 A1 | 11/2007 | Igaki |
| 2008/0071343 A1 | 3/2008 | Mayberry et al. |
| 2008/0172122 A1 | 7/2008 | Mayberry et al. |
| 2009/0105806 A1 | 4/2009 | Benjamin et al. |
| 2009/0216315 A1 | 8/2009 | Schreck et al. |
| 2009/0259298 A1 | 10/2009 | Mayberry et al. |

| | | | |
|---|---|---|---|
| 2010/0004730 A1 | 1/2010 | Benjamin et al. | |
| 2010/0179638 A1 | 7/2010 | Shaolian et al. | |
| 2011/0054586 A1 | 3/2011 | Mayberry et al. | |
| 2011/0054587 A1 | 3/2011 | Mayberry et al. | |
| 2011/0054594 A1 | 3/2011 | Mayberry et al. | |

FOREIGN PATENT DOCUMENTS

| | | |
|---|---|---|
| EP | 0 621 015 A1 | 10/1994 |
| EP | 0 688 545 | 12/1995 |
| EP | 747 020 A2 | 2/1996 |
| EP | 0 740 928 A2 | 11/1996 |
| EP | 0 782 841 | 7/1997 |
| EP | 0 783 873 A2 | 7/1997 |
| EP | 0 783 874 A2 | 7/1997 |
| EP | 0696447 B1 | 1/2000 |
| EP | 0 732 088 B1 | 4/2000 |
| EP | 1 433 438 | 6/2004 |
| ES | 1 038 606 | 7/1998 |
| JP | 04-25755 | 1/1992 |
| WO | WO 94/24961 | 11/1994 |
| WO | WO 96/34580 | 11/1996 |
| WO | WO 97/10757 | 3/1997 |
| WO | 98/20812 A | 5/1998 |
| WO | WO 9827894 | 7/1998 |
| WO | WO 99/58084 | 5/1999 |
| WO | WO 99/44536 | 9/1999 |
| WO | WO 99/47077 | 9/1999 |
| WO | WO 00/53251 A | 9/2000 |
| WO | WO 01/03762 A | 1/2001 |
| WO | WO 02/060345 A | 8/2002 |
| WO | WO 2005/037076 | 4/2005 |

OTHER PUBLICATIONS

Supplemental European Search Report Application EP 03 79 0040 mailed on Aug. 21, 2007.

Japanese Office Action dated Nov. 16, 2010; JP Application No. 2004-555731.

Japanese Office Action dated Apr. 13, 2010; JP Application No. 2004-555731.

Japanese Office Action dated May 26, 2009; JP Application No. 2004-555731.

European Exam Report, re EP Application No. EP 03 79 0040, dated Aug. 27, 2009.

US 6,413,270, 07/2002, Thornton et al. (withdrawn)

* cited by examiner

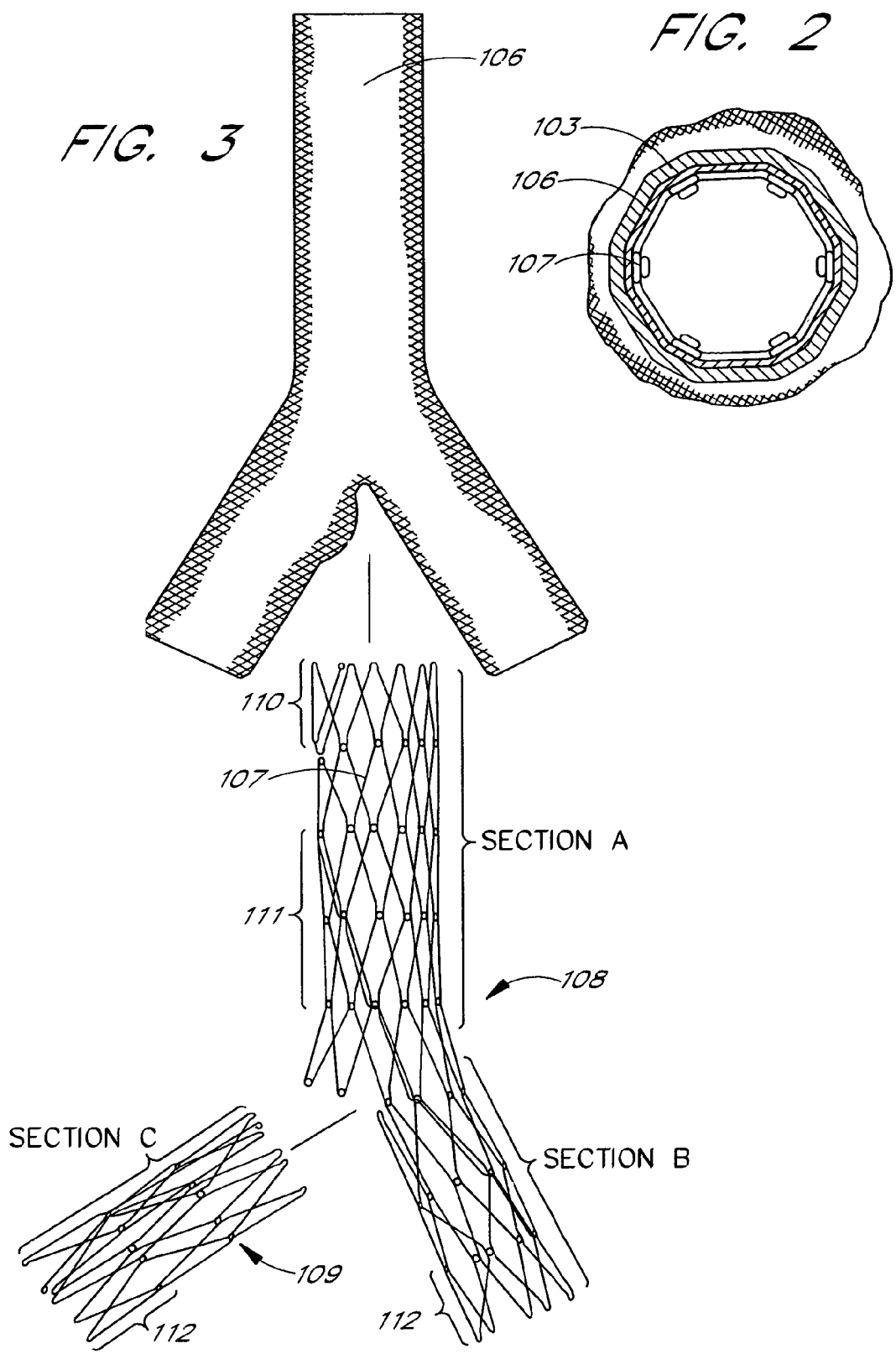

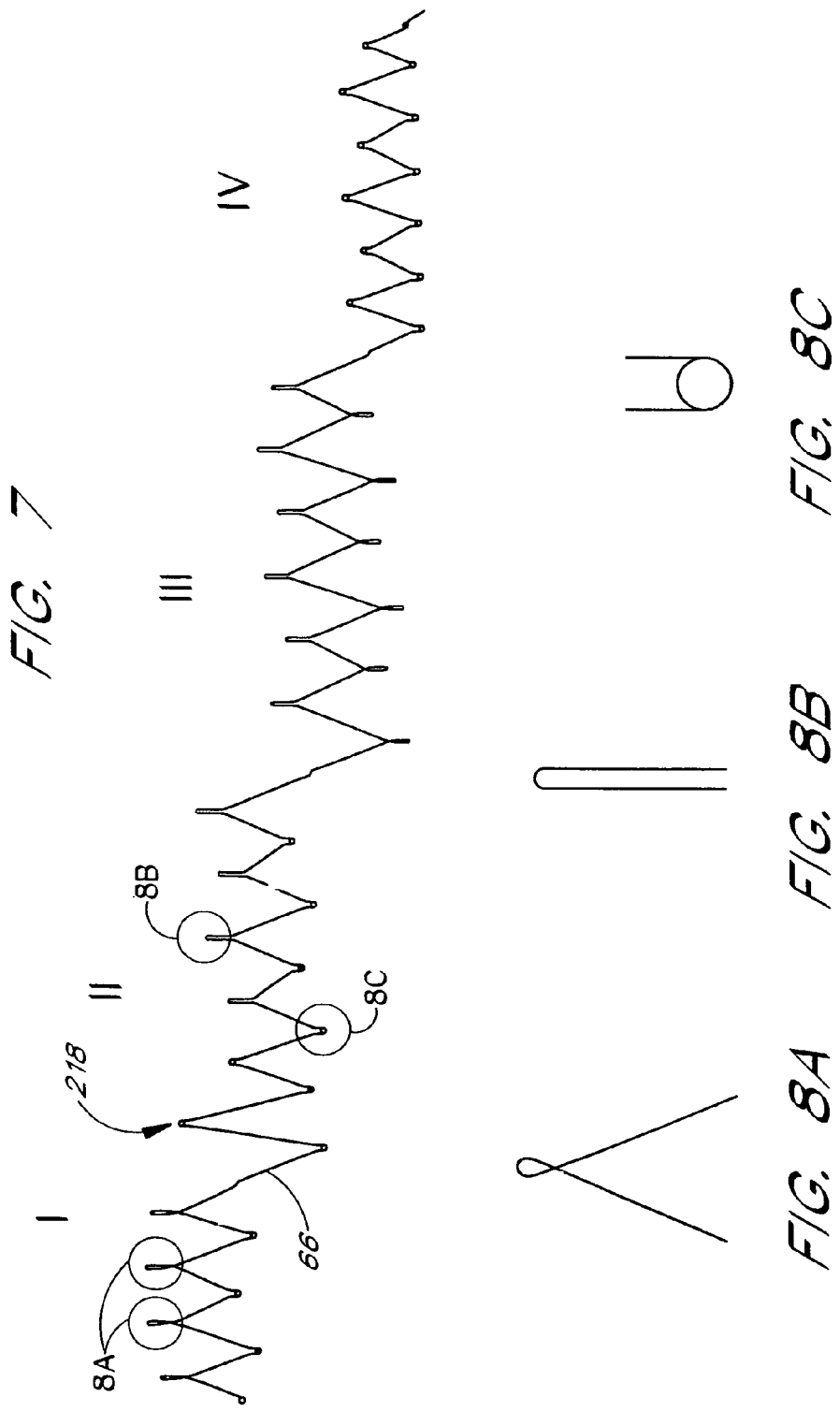

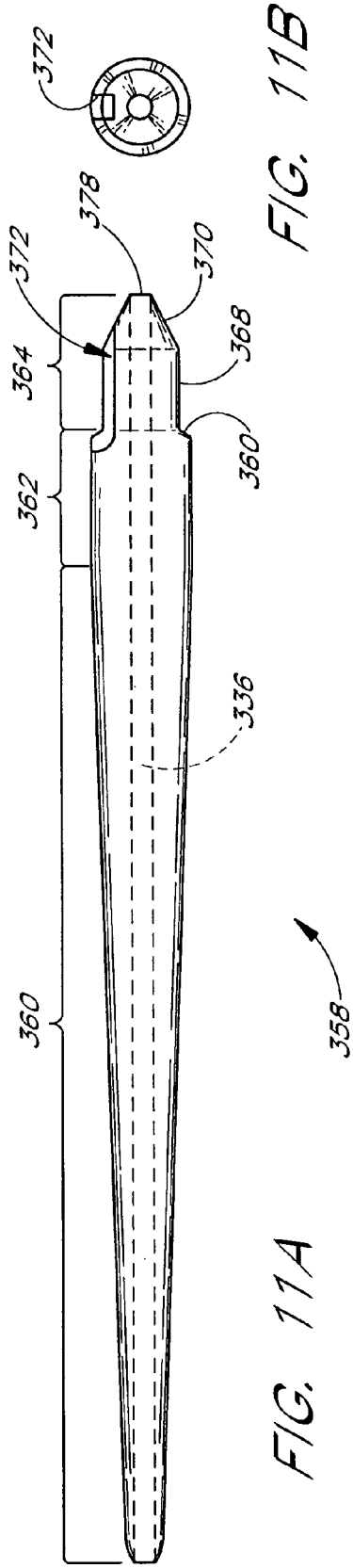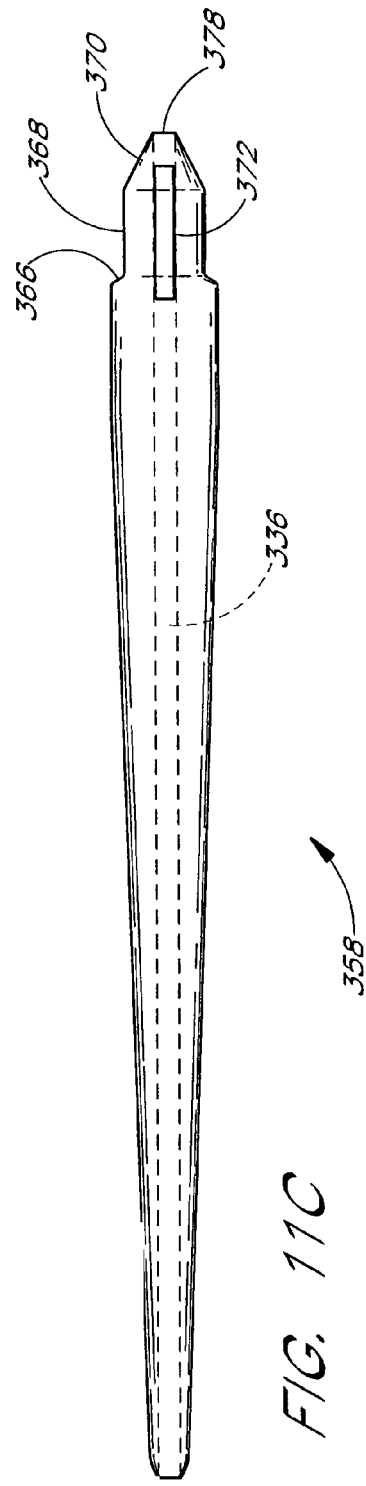

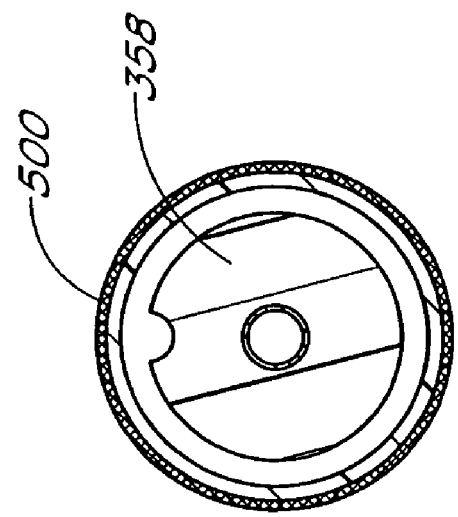
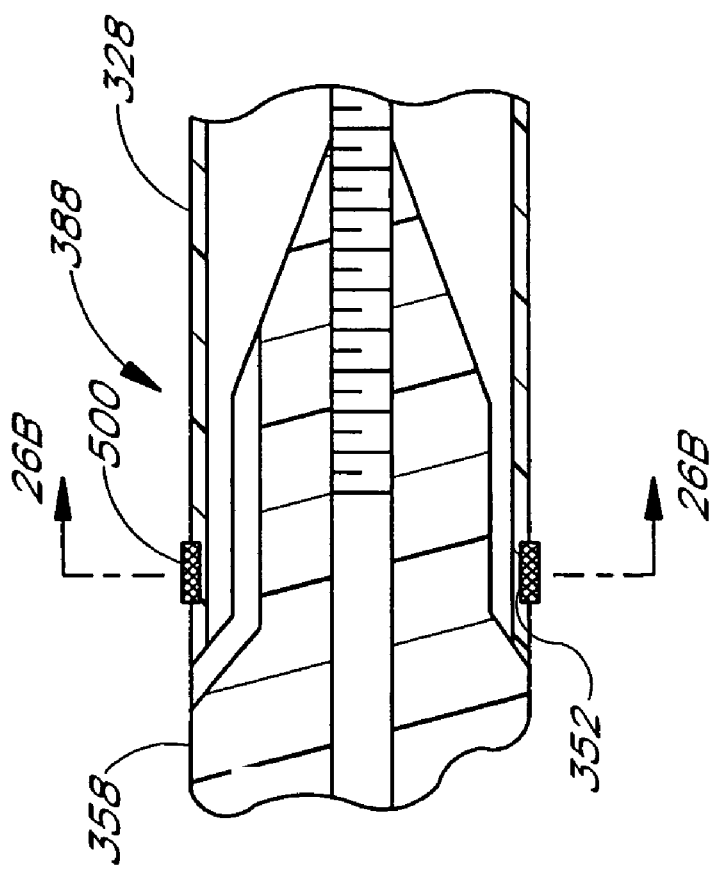

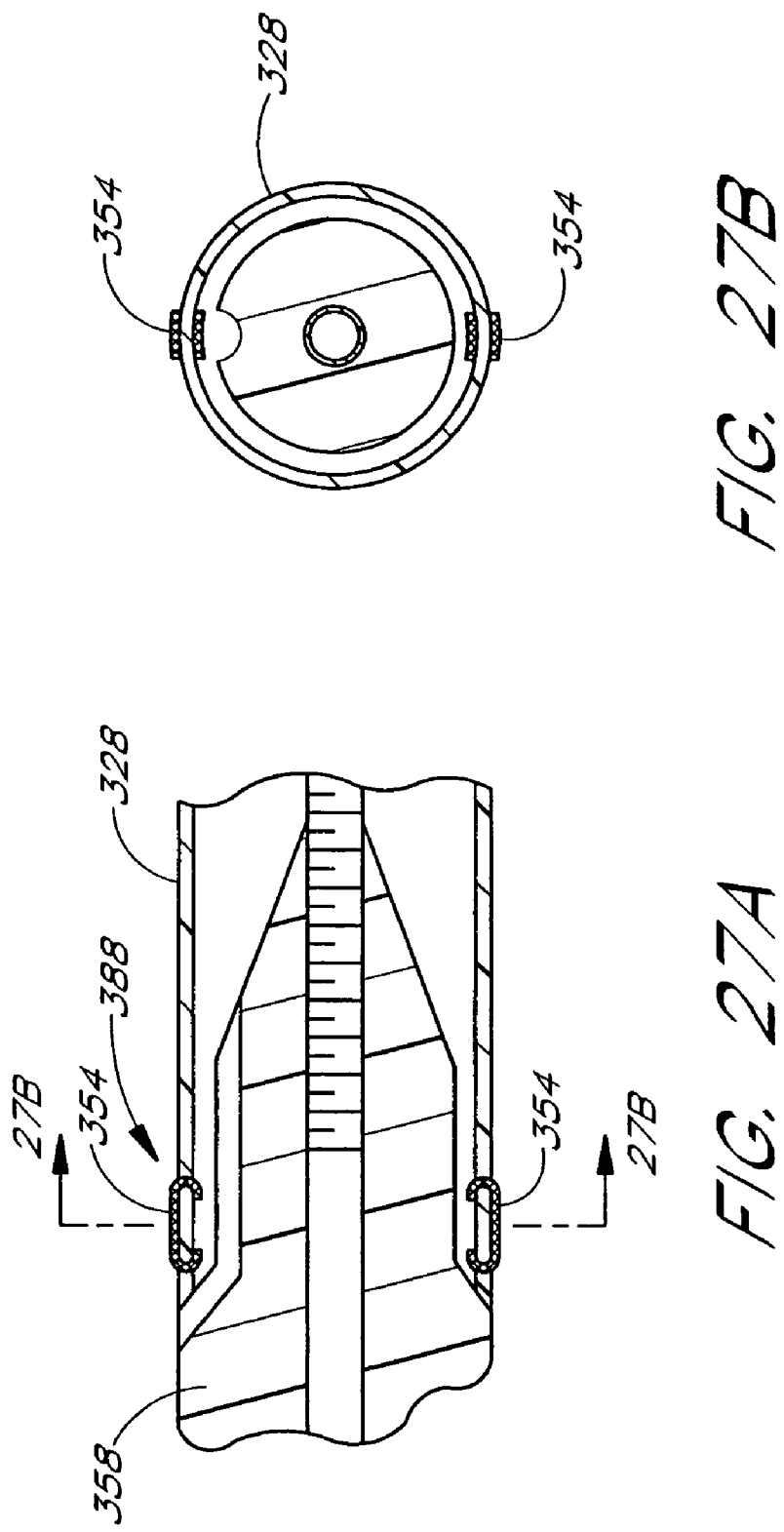

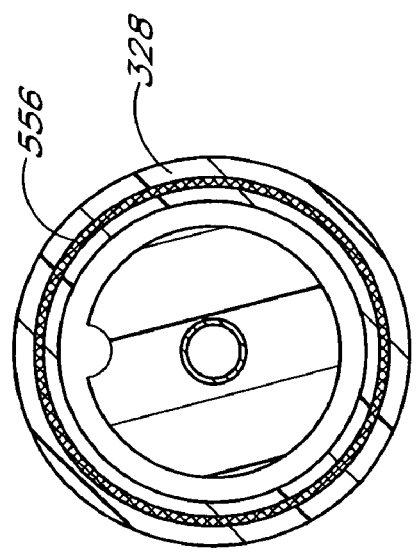
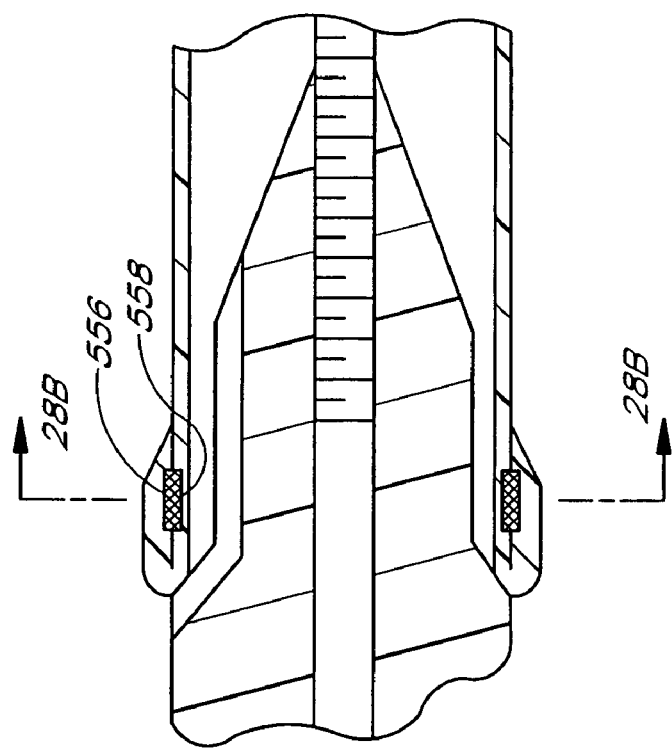
FIG. 28B
FIG. 28A

GRAFT DEPLOYMENT SYSTEM

PRIORITY INFORMATION

This application is a continuation in part of U.S. patent application Ser. No. 09/795,993, filed Feb. 28, 2001, now U.S. Pat. No. 6,663,665, which is a divisional of U.S. patent application Ser. No. 09/266,661, filed Mar. 11, 1999, entitled "Singled Puncture Bifurcation Graft Deployment System", now U.S. Pat. No. 6,261,316 and this application claims the priority benefit under 35 U.S.C. §119(e) of Provisional Application 60/429,666 filed Nov. 26, 2002.

BACKGROUND OF THE INVENTION

Description of the Related Art

An abdominal aortic aneurysm is a sac caused by an abnormal dilation of the wall of the aorta, a major artery of the body, as it passes through the abdomen. The abdomen is that portion of the body which lies between the thorax and the pelvis. It contains a cavity, known as the abdominal cavity, separated by the diaphragm from the thoracic cavity and lined with a serous membrane, the peritoneum. The aorta is the main trunk, or artery, from which the systemic arterial system proceeds. It arises from the left ventricle of the heart, passes upward, bends over and passes down through the thorax and through the abdomen to about the level of the fourth lumbar vertebra, where it divides into the two common iliac arteries.

The aneurysm usually arises in the infrarenal portion of the diseased aorta, for example, below the kidneys. When left untreated, the aneurysm may eventually cause rupture of the sac with ensuing fatal hemorrhaging in a very short time. High mortality associated with the rupture led initially to transabdominal surgical repair of abdominal aortic aneurysms. Surgery involving the abdominal wall, however, is a major undertaking with associated high risks. There is considerable mortality and morbidity associated with this magnitude of surgical intervention, which in essence involves replacing the diseased and aneurysmal segment of blood vessel with a prosthetic device which typically is a synthetic tube, or graft, usually fabricated of Polyester, Urethane, DACRON™, TEFLON™, or other suitable material.

To perform the surgical procedure requires exposure of the aorta through an abdominal incision which can extend from the rib cage to the pubis. The aorta must be closed both above and below the aneurysm, so that the aneurysm can then be opened and the thrombus, or blood clot, and arteriosclerotic debris removed. Small arterial branches from the back wall of the aorta are tied off. The DACRON™ tube, or graft, of approximately the same size of the normal aorta is sutured in place, thereby replacing the aneurysm. Blood flow is then reestablished through the graft. It is necessary to move the intestines in order to get to the back wall of the abdomen prior to clamping off the aorta.

If the surgery is performed prior to rupturing of the abdominal aortic aneurysm, the survival rate of treated patients is markedly higher than if the surgery is performed after the aneurysm ruptures, although the mortality rate is still quite high. If the surgery is performed prior to the aneurysm rupturing, the mortality rate is typically slightly less than 10%. Conventional surgery performed after the rupture of the aneurysm is significantly higher, one study reporting a mortality rate of 66.5%. Although abdominal aortic aneurysms can be detected from routine examinations, the patient does not experience any pain from the condition. Thus, if the patient is not receiving routine examinations, it is possible that the aneurysm will progress to the rupture stage, wherein the mortality rates are significantly higher.

Disadvantages associated with the conventional, prior art surgery, in addition to the high mortality rate include the extended recovery period associated with such surgery; difficulties in suturing the graft, or tube, to the aorta; the loss of the existing aorta wall and thrombosis to support and reinforce the graft; the unsuitability of the surgery for many patients having abdominal aortic aneurysms; and the problems associated with performing the surgery on an emergency basis after the aneurysm has ruptured. A patient can expect to spend from one to two weeks in the hospital after the surgery, a major portion of which is spent in the intensive care unit, and a convalescence period at home from two to three months, particularly if the patient has other illnesses such as heart, lung, liver, and/or kidney disease, in which case the hospital stay is also lengthened. The graft must be secured, or sutured, to the remaining portion of the aorta, which may be difficult to perform because of the thrombosis present on the remaining portion of the aorta. Moreover, the remaining portion of the aorta wall is frequently friable, or easily crumbled.

Since many patients having abdominal aortic aneurysms have other chronic illnesses, such as heart, lung, liver, and/or kidney disease, coupled with the fact that many of these patients are older, the average age being approximately 67 years old, these patients are not ideal candidates for such major surgery.

More recently, a significantly less invasive clinical approach to aneurysm repair, known as endovascular grafting, has been developed. Parodi, et al. provide one of the first clinical descriptions of this therapy. Parodi, J. C., et al., "Transfemoral Intraluminal Graft Implantation for Abdominal Aortic Aneurysms," 5 Annals of Vascular Surgery 491 (1991). Endovascular grafting involves the transluminal placement of a prosthetic arterial graft within the lumen of the artery.

In general, transluminally implantable prostheses adapted for use in the abdominal aorta comprise a tubular wire cage surrounded by a tubular PTFE or Dacron sleeve. Both balloon expandable and self expandable support structures have been proposed. Endovascular grafts adapted to treat both straight segment and bifurcation aneurysms have also been proposed.

Notwithstanding the foregoing, there remains a need for a structurally simple, easily deployable transluminally implantable endovascular prosthesis, with a support structure adaptable to span either a straight or bifurcated abdominal aortic aneurysm. Preferably, the tubular prosthesis can be self expanded at the site to treat the abdominal aortic aneurysm, and exhibits flexibility to accommodate nonlinear anatomies and normal anatomical movement.

SUMMARY OF THE INVENTION

Accordingly, one embodiment a bifurcation graft deployment system, comprises an elongate, flexible catheter body, having a proximal end and a distal end and comprising an outer sheath and an inner core that is axially moveable with respect to the outer sheath. A main vessel graft restraint comprising a first peelable cover for restrains a main vessel portion of a bifurcated graft. A first branch vessel graft restraint restrains a first branch vessel portion of the graft. A second branch vessel graft restraint restrains a second branch vessel portion of the graft. The first peelable cover is coupled to a main branch release element and wherein each of the main vessel graft restraint, first branch vessel graft restraint, and the second branch vessel graft restraint are positioned within the catheter body in a graft loaded condition.

Another embodiment comprises a method for deploying a bifurcated endoluminal prosthesis at the junction of a main vessel and first and second branch vessels. The method comprises providing a deployment system containing a prosthesis having a main body section and first and second proximally extending branch sections, introducing the deployment system into the first branch vessel at a first access site, advancing the deployment system distally through at least a portion of the first branch vessel and into the main vessel, releasing the second branch section of the prosthesis by proximally retracting an outer sheath of the deployment system, expanding the main body section of the prosthesis from a radially compressed state within the deployment system to a radially expanded state within the main vessel by removing a first peelable sheath from the main branch section, and expanding the second branch section within the second branch vessel by proximally retracting a second branch release wire.

Another embodiment involves deployment system for deploying a bifurcated prosthesis at the junction of a main vessel and first and second branch vessels. The system includes a delivery catheter having an inner core, an outer sheath and a distal tip that is coupled to the inner core, the inner core being slidably engaged within the outer sheath. A bifurcated prosthesis has a main body section with proximal and distal ends, and first and second branch sections at the proximal end of the main body section. The main body section is held in a radially compressed state by a first peelable cover. The first branch section is held in a radially compressed state within a first tubular cover and the second branch section is also held in a radially compressed within a second tubular cover.

Another embodiment involves a method for deploying a straight tube endoluminal prosthesis. The method comprises providing a deployment system containing a straight tube prosthesis including a distal section and a proximal section, introducing the deployment system into a vessel at an access site, advancing the deployment system distally through the vessel, proximally retracting an outer sheath of the deployment system to expose the prosthesis, and expanding at least a portion of the prosthesis from a radially compressed state within the deployment system to a radially expanded state within the vessel by proximately retracting a first release element so as to tear a peelable cover.

These embodiments are intended to be within the scope of the invention herein disclosed. These and other embodiments of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 2 is a cross-sectional view of the implanted graft taken along the lines 2-2 of FIG. 1.

FIG. 3 is an exploded view of the bifurcated vascular prosthesis in accordance with the present invention, showing a two-part self expandable wire support structure separated from an outer tubular sleeve.

FIG. 7 is a plan view of formed wire useful for rolling about an axis to form a branch support structure in accordance with the three-part support embodiment of the present invention shown in FIG. 5.

FIGS. 8A, 8B and 8C are enlargements of the apexes delineated by lines A, B and C, respectively, in FIG. 7.

FIGS. 11A,B and C are side, top and rear views of a distal tip of the bifurcated delivery catheter shown in FIG. 9A.

FIG. 26A is a close view of portion 26A of FIG. 9B.

FIG. 26B is a cross-sectional view taken through line 26B-26B of FIG. 26A.

FIG. 27A is a modified embodiment of the portion shown in FIG. 26A.

FIG. 27B is a cross-sectional view taken through line 27B-27B of FIG. 26A.

FIG. 28A is another modified embodiment of the portion shown in FIG. 26A.

FIG. 28B is a cross-sectional view taken through line 28B-28B of FIG. 26A

DETAILED DESCRIPTION OF THE PREFERRED EMBODIMENT

Figure 1:
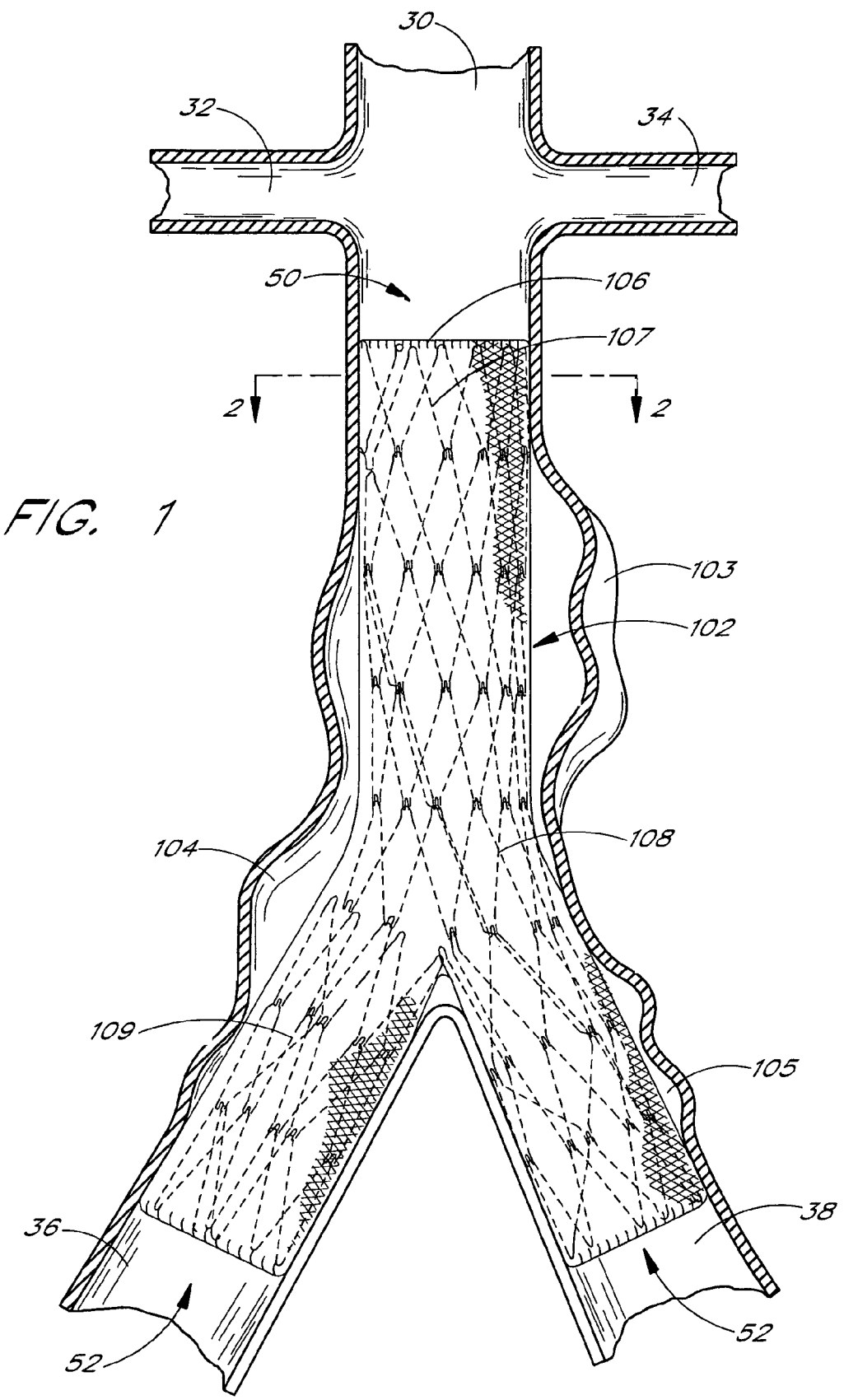
FIG. 1 is a schematic representation of a bifurcated vascular prosthesis in accordance with the present invention, positioned at the bifurcation between the abdominal aorta and the right and left common iliac arteries.

Referring to FIG. 1, there is disclosed a schematic representation of the abdominal part of the aorta and its principal branches. In particular, the abdominal aorta 30 is characterized by a right renal artery 32 and left renal artery 34. The large terminal branches of the aorta are the right and left common iliac arteries 36 and 38. Additional vessels (e.g., second lumbar, testicular, inferior mesenteric, middle sacral) have been omitted for simplification.

An expanded bifurcated endoluminal vascular prosthesis 102, in accordance with one embodiment of the present invention, is illustrated spanning aneurysms 103, 104 and 105. It should be appreciated that the illustrated prosthesis 102 and the other prosthesis configurations disclosed herein are only examples of prostheses that are deployable using the devices and methods of the present invention. Moreover, as will be apparent to those of skill in the art in view of the disclosure herein, these devices and methods may be used to deploy essentially any self expandable bifurcated or straight segment prosthesis, The illustrated endoluminal vascular prosthesis 102 includes a polymeric sleeve 106 and a tubular wire support 107, illustrated in situ in FIG. 1. The sleeve 106 and wire support 107 are more readily visualized in the exploded view shown in FIG. 3. The endoluminal prosthesis 102 illustrated and described herein depicts an embodiment in which the polymeric sleeve 106 is situated concentrically outside of the tubular wire support 107. However, other embodiments may include a sleeve situated instead concentrically inside the wire support or on both of the inside and the outside of the wire support. Alternatively, the wire support may be embedded within a polymeric matrix or layer which makes up the sleeve. Regardless of whether the sleeve 106 is inside or outside the wire support 107, the sleeve may be attached to the wire support by any of a variety of means, as has been previously discussed.

The tubular wire support 107 comprises a primary component 108 for traversing the aorta and a first iliac, and a branch component 109 for extending into the second iliac. The primary component 108 may be formed from a continuous single length of wire, throughout both the aorta trunk portion and the iliac branch portion. See FIGS. 3 and 4. Alternatively, each iliac branch component can be formed separately from the aorta trunk portion. Construction of the graft from a three part cage conveniently facilitates the use of different gauge wire in the different components (e.g. 0.014" diameter main trunk and 0.012" diameter branch components).

Figure 4:
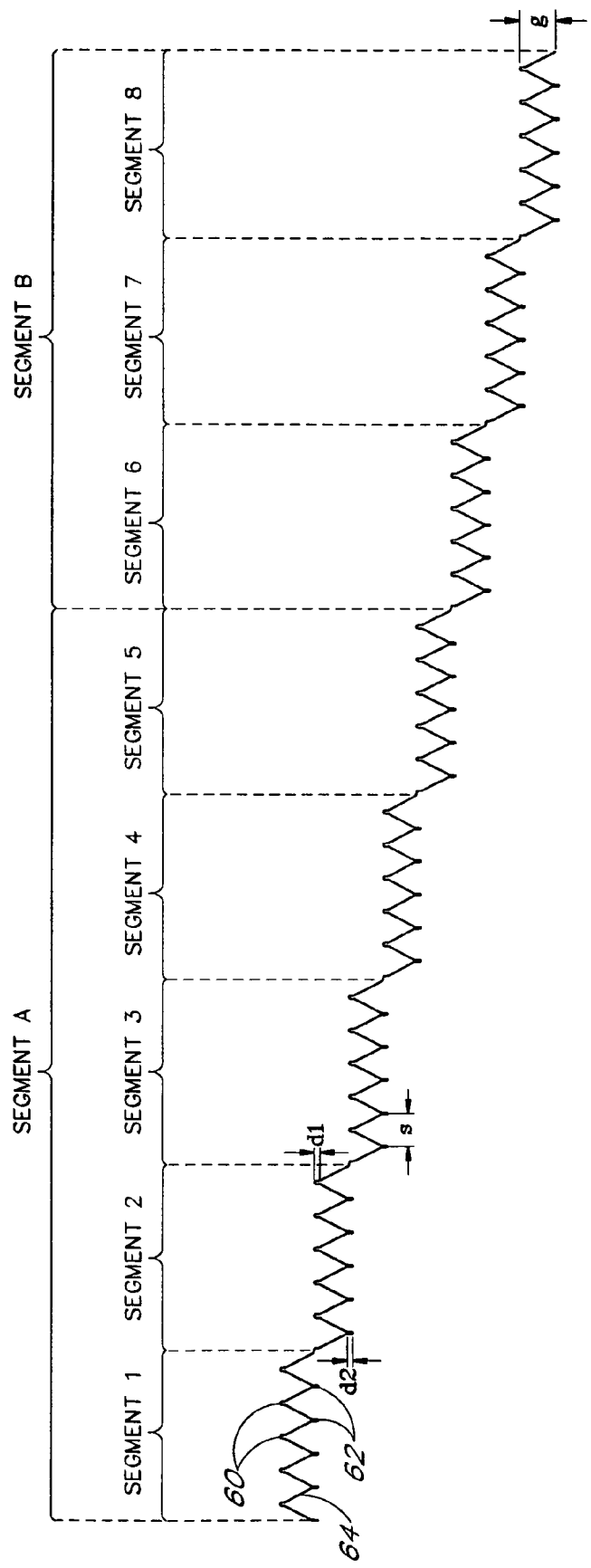
FIG. 4 is a plan view of formed wire useful for rolling about an axis into an aortic trunk segment and a first iliac branch segment support structure in accordance with the present invention.

The wire support 107 is preferably formed in a plurality of discrete segments, connected together and oriented about a common axis. In FIG. 4, Section A corresponds to the aorta trunk portion of the primary component 108, and includes segments 1-5. Segments 6-8 (Section B) correspond to the iliac branch portion of the primary component 108.

In general, each of the components of the tubular wire support 107 can be varied considerably in diameter, length, and expansion coefficient, depending upon the intended application. For implantation within a typical adult, the aorta trunk portion (section A) of primary component 108 will have a length within the range of from about 5 cm to about 12 cm, and, typically within the range of from about 9 cm to about 10 cm. The unconstrained outside expanded diameter of the section A portion of the primary component 108 will typically be within the range of from about 20 mm to about 40 mm. The unconstrained expanded outside diameter of the section A portion of primary component 108 can be constant or substantially constant throughout the length of section A, or can be tapered from a relatively larger diameter at the proximal end to a relatively smaller diameter at the bifurcation. In general, the diameter of the distal end of section A will be on the order of no more than about 95% and, preferably, no more than about 85% of the diameter of the proximal end of section A.

The right and left iliac portions, corresponding to section B on primary component 108 and section C will typically be bilaterally symmetrical. Section C length will generally be within the range of from about 1 cm to about 5 cm, and section C diameter will typically be within the range of from about 10 mm to about 20 mm.

Referring to FIG. 3, the wire cage 107 is dividable into a proximal zone 110, a central zone 111 and a distal zone 112. In addition, the wire cage 107 can have a transitional tapered and or stepped diameter within a given zone. Further details of the bifurcated and straight segment grafts in accordance with the present invention are disclosed in copending U.S. patent application Ser. No. 09/251,363 filed Feb. 17, 1999 and entitled Articulated Bifurcation Graft, the disclosure of which is incorporated in its entirety herein by reference.

Referring to FIG. 4, there is illustrated a plan view of the single formed wire used for rolling about a longitudinal axis to produce a primary segment 108 having a five segment aorta section and a three segment iliac section. The formed wire exhibits distinct segments, each corresponding to an individual tubular segment in the tubular support. Additional details of the wire cage layout and construction can be found in copending U.S. patent application Ser. No. 09/034,689 entitled Endoluminal Vascular Prosthesis, filed Mar. 4, 1998, the disclosure of which is incorporated in its entirety herein by reference.

Each segment has a repeating pattern of proximal bends 60 connected to corresponding distal bends 62 by wall sections 64 which extend in a generally zig-zag configuration when the segment is radially expanded. Each segment is connected to the adjacent segment through a connector 66, and one or more links 70 (see FIG. 6). The connector 66 in the illustrated embodiment comprises two wall sections 64 which connect a proximal bend 60 on a first segment with a distal bend 62 on a second, adjacent segment. The connector 66 may additionally be provided with a connector bend 68, which may be used to impart increased radial strength to the graft and/or provide a tie site for a circumferentially extending suture.

In the illustrated embodiment, section A is intended for deployment within the aorta whereas section B is intended to be deployed within a first iliac. Thus, section B will preferably have a smaller expanded diameter than section A. This may be accomplished by providing fewer proximal and distal bends 60, 62 per segment in section B or in other manners as will be apparent to those of skill in the art in view of the disclosure herein. In the illustrated embodiment, section B has one fewer proximal bend 60 per segment than does each segment in section A. This facilitates wrapping of the wire into a tubular prosthesis cage such as that illustrated in FIG. 3, so that the iliac branch has a smaller diameter than the aorta branch. At the bifurcation, an opening remains for connection of the second iliac branch. The second branch is preferably formed from a section of wire in accordance with the general principles discussed above, and in a manner that produces a similarly dimensioned wire cage as that produced by section B. The second iliac branch (section C) may be attached at the bifurcation to section A and/or section B in any of a variety of manners, to provide a secure junction therebetween. In one embodiment, one or two of the proximal bends 60 on section C will be secured to the corresponding distal bends 62 on the distal most segment of section A. Attachment may be accomplished such as through the use of a circumferentially threaded suture, through links 70 as has been discussed previously, through soldering or other attachment means. The attachment means will be influenced by the desired flexibility of the graft at the bifurcation, which will in turn be influenced by the method of deployment of the vascular graft as will be apparent to those of skill in the art in view of the disclosure herein.

Figure 5:
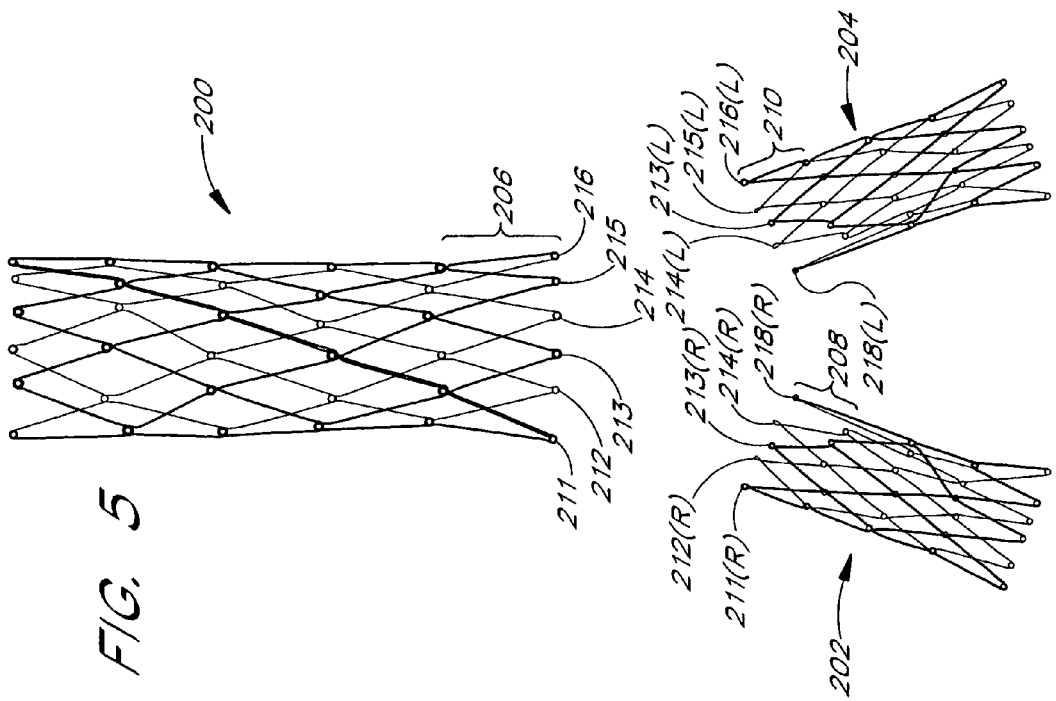
FIG. 5 is a schematic representation of another embodiment of the wire support structure for the bifurcated vascular prosthesis of the present invention, showing a main body support structure and separate branch support structures.

Referring to FIG. 5, there is disclosed an exploded schematic representation of a hinged or articulated variation in the tubular wire support structure for a bifurcated graft in accordance with present invention. The tubular wire support comprises a main body, or aortic trunk portion 200 and right 202 and left 204 iliac branch portions. Right and left designations correspond to the anatomic designations of right and left common iliac arteries. The proximal end 206 of the aortic trunk portion 200 has apexes 211-216 adapted for connection with the complementary apexes on the distal ends 208 and 210 of the right 202 and left 204 iliac branch portions, respectively. Complementary pairing of apexes is indicated by the shared numbers, wherein the right branch portion apexes are designated by (R) and the left branch portion apexes are designated by (L). Each of the portions may be formed from a continuous single length of wire. See FIG. 7.

Figure 6:
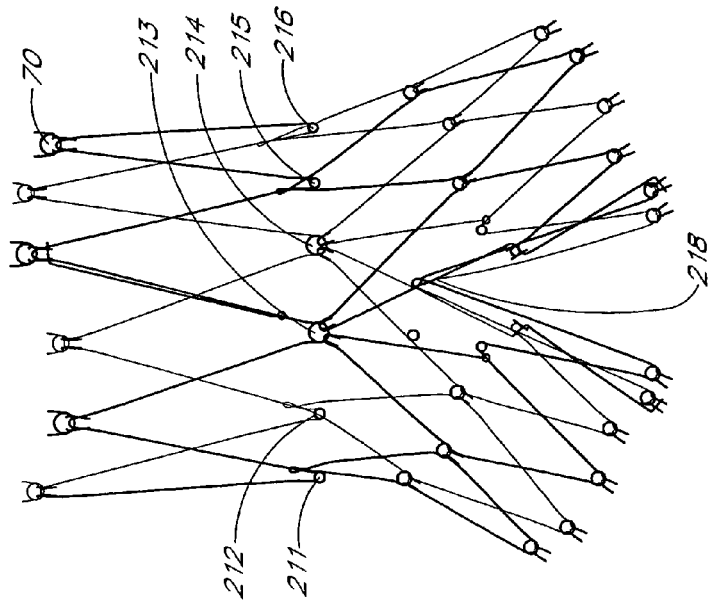
FIG. 6 is a schematic representation of the three-part wire support structure as in FIG. 5, illustrating the sliding articulation between the branch supports and the main body support.

Referring to FIG. 6, the assembled articulated wire support structure is shown. The central or medial apex 213 in the foreground (anterior) of the aortic trunk portion 200 is linked with 213(R) on the right iliac portion 202 and 213(L) on the left iliac portion 204. Similarly, the central apex 214 in the background (posterior) is linked with 214 (R) on the right iliac portion 202 and 214(L) on the left iliac portion 204. Each of these linkages has two iliac apexes joined with one aortic branch apex. The medial most apexes 218 (R) and (L) of the iliac branch portions 202 and 204 are linked together, without direct connection with the aortic truck portion 200.

The medial apexes 213 and 214 function as pivot points about which the right and left iliac branches 202, 204 can pivot to accommodate unique anatomies. Although the right and left iliac branches 202, 204 are illustrated at an angle of about 45° to each other, they are articulable through at least an angle of about 90° and preferably at least about 120°. The illustrated embodiment allows articulation through about 180° while maintaining patency of the central lumen. To further improve patency at high iliac angles, the apexes 213 and 214 can be displaced proximally from the transverse plane which roughly contains apexes 211, 212, 215 and 216 by a minor adjustment to the fixture about which the wire is formed. Advancing the pivot point proximally relative to the lateral apexes (e.g., 211, 216) opens the unbiased angle between the iliac branches 202 and 204.

In the illustrated embodiment, the pivot point is formed by a moveable link between an eye on apex 213 and two apexes 213R and 213L folded therethrough. To accommodate the two iliac apexes 213R and 213L, the diameter of the eye at apex 213 may be slightly larger than the diameter of the eye on other apexes throughout the graft. Thus, for example, the diameter of the eye at apex 213 in one embodiment made from 0.014" diameter wire is about 0.059", compared to a diameter of about 0.020" for eyes elsewhere in the graft.

Although the pivot points (apexes 213, 214) in the illustrated embodiment are on the medial plane, they may be moved laterally such as, for example, to the axis of each of the iliac branches. In this variation, each iliac branch will have an anterior and a posterior pivot link on or about its longitudinal axis, for a total of four unique pivot links at the bifurcation. Alternatively, the pivot points can be moved as far as to lateral apexes 211 and 216. Other variations will be apparent to those of skill in the art in view of the disclosure herein.

To facilitate lateral rotation of the iliac branches 202, 204 about the pivot points and away from the longitudinal axis of the aorta trunk portion 200 of the graft, the remaining links between the aorta trunk portion 200 and the iliac branches 202, 204 preferably permit axial compression and expansion. In general, at least one and preferably several links lateral to the pivot point in the illustrated embodiment permit axial compression or shortening of the graft to accommodate lateral pivoting of the iliac branch. If the pivot point is moved laterally from the longitudinal axis of the aorta portion of the graft, any links medial of the pivot point preferably permit axial elongation to accommodate lateral rotation of the branch. In this manner, the desired range of rotation of the iliac branches may be accomplished with minimal deformation of the wire, and with patency of the graft optimized throughout the angular range of motion.

To permit axial compression substantially without deformation of the wire, the lateral linkages, 211 and 212 for the right iliac, and 215 and 216 for the left iliac, may be different from the previously described apex-to-apex linkage configurations. The lateral linkages are preferably slideable linkages, wherein a loop formed at the distal end of the iliac apex slidably engages a strut of the corresponding aortic truck portion. The loop and strut orientation may be reversed, as will be apparent to those of skill in the art. Interlocking "elbows" without any distinct loop may also be used. Such an axially compressible linkage on the lateral margins of the assembled wire support structure allow the iliac branch portions much greater lateral flexibility, thereby facilitating placement in patients who often exhibit a variety of iliac branch asymmetries and different angles of divergence from the aortic trunk.

Referring to FIG. 7, there is illustrated a plan view of a single formed wire used for rolling about a longitudinal axis to produce a four segment straight tubular wire support for an iliac limb. The formed wire exhibits distinct segments, each corresponding to an individual tubular segment in the tubular supports 202 or 204 (See FIG. 5). The distal segment I, is adapted to articulate with the aortic trunk portion 200 and the adjacent iliac limb portion. The distal segment (I) has two apexes (e.g. corresponding to 211 and 212 on the right iliac portion 202 in FIG. 5) which form a loop adapted to slidably engage a strut in the lateral wall of the aortic portion. These articulating loops (A) are enlarged in FIG. 8A. As discussed above, the loops are preferably looped around a strut on the corresponding apex of the proximal aortic segment to provide a sliding linkage.

The apex 218 is proximally displaced relative to the other four apexes in the distal segment (I). Apex 218 (R or L) is designed to link with the complementary 218 apex on the other iliac branch portion (See FIG. 6). The apex 218 in the illustrated embodiment is formed adjacent or near an inter-segment connector 66, which extends proximally from the distal segment.

The other apexes on the distal segment (I) of an iliac limb are designed to link with a loop on the corresponding apex of the proximal aortic segment. Because many variations of this linkage are consistent with the present invention the form of the corresponding apexes may vary. In a preferred variation, the apexes (B) form a narrow U-shape, having an inside diameter of about 0.019 inches in an embodiment made from 0.012 inch Conichrome wire (tensile strength 300 ksi minimum) as illustrated in FIG. 8B. The U-shaped, elongated axial portion of the apex shown in FIG. 8B permits the apex to be wrapped through and around a corresponding loop apex of the proximal aortic segment.

In more general terms, the wire support illustrated in FIGS. 5 and 6 comprises a main body support structure formed from one or more lengths of wire and having a proximal end, a distal end and a central lumen extending along a longitudinal axis. The wire support also comprises a first branch support structure formed from one or more lengths of wire and having a proximal end, a distal end and a central lumen therethrough. The first branch support structure is pivotably connected to the proximal end of the main body support structure. The tubular wire support further comprises a second branch support structure formed from one or more lengths of wire and having a proximal end, a distal end and a central lumen extending therethrough. The distal end of the second branch support structure is pivotably connected to the proximal end of the main body support structure.

Further, the distal ends of the first and second branch structures may be joined together by a flexible linkage, formed for example between apexes 218(R) and 218(L) in FIG. 5. By incorporating a medial linkage between the two branch support structures and pivotable linkages with the main trunk, the first and second branch support structures can hinge laterally outward from the longitudinal axis without compromising the volume of the lumen. Thus, the branches may enjoy a wide range of lateral movement, thereby accommodating a variety of patient and vessel heterogeneity. Additional corresponding apexes between the main trunk and each iliac branch may also be connected, or may be free floating within the outer polymeric sleeve. Axially compressible lateral linkages, discussed above and illustrated in FIG. 6, may optionally be added.

The proximal apexes (C) of the iliac limb portions are adapted to link with the distal apexes of the next segment. These proximal apexes preferably form loops, such as those illustrated in FIG. 8C, wherein the elongated axial portions of the corresponding proximal apex in the adjacent segment can wrap around the loop, thereby providing flexibility of the graft.

The wire may be made from any of a variety of different alloys and wire diameters or non-round cross-sections, as has been discussed. In one embodiment of the bifurcation graft, the wire gauge remains substantially constant throughout section A of the primary component 49 and steps down to a second, smaller cross-section throughout section B of primary component 108.

A wire diameter of approximately 0.018 inches may be useful in the aorta trunk portion of a graft having five segments each having 2.0 cm length per segment, each segment having six struts intended for use in the aorta, while a smaller diameter such as 0.012 inches might be useful for segments of the graft having 6 struts per segment intended for the iliac artery.

In one embodiment of the present invention, the wire diameter may be tapered throughout from the proximal to distal ends of the section A and/or section B portions of the primary component 108. Alternatively, the wire diameter may be tapered incremental or stepped down, or stepped up, depending on the radial strength requirements of each particular clinical application. In one embodiment, intended for the abdominal aortic artery, the wire has a cross-section of about 0.018 inches in the proximal zone 110 and the wire tapers down regularly or in one or more steps to a diameter of about 0.012 inches in the distal zone 112 of the graft 102. End point dimensions and rates of taper can be varied widely, within the spirit of the present invention, depending upon the desired clinical performance.

In general, in the tapered or stepped wire embodiments, the diameter of the wire in the iliac branches is no more than about 80% of the diameter of the wire in the aortic trunk. This permits increased flexibility of the graft in the region of the iliac branches, which has been determined by the present inventors to be clinically desirable.

The collapsed prosthesis in accordance with the present invention has a diameter in the range of about 2 mm to about 10 mm. Preferably, the maximum diameter of the collapsed prosthesis is in the range of about 3 mm to 6 min (12 to 18 French). Some embodiments of the delivery catheter including the prosthesis will be in the range of from 18 to 20 or 21 French; other embodiments will be as low as 19 F, 16 F, 14 F, or smaller. After deployment, the expanded endoluminal vascular prosthesis has radially self-expanded to a diameter anywhere in the range of about 20 to 40 mm, corresponding to expansion ratios of about 1:2 to 1:20. In a preferred embodiment, the expansion ratios range from about 1:4 to 1:8, more preferably from about 1:4 to 1:6.

Figure 9A:
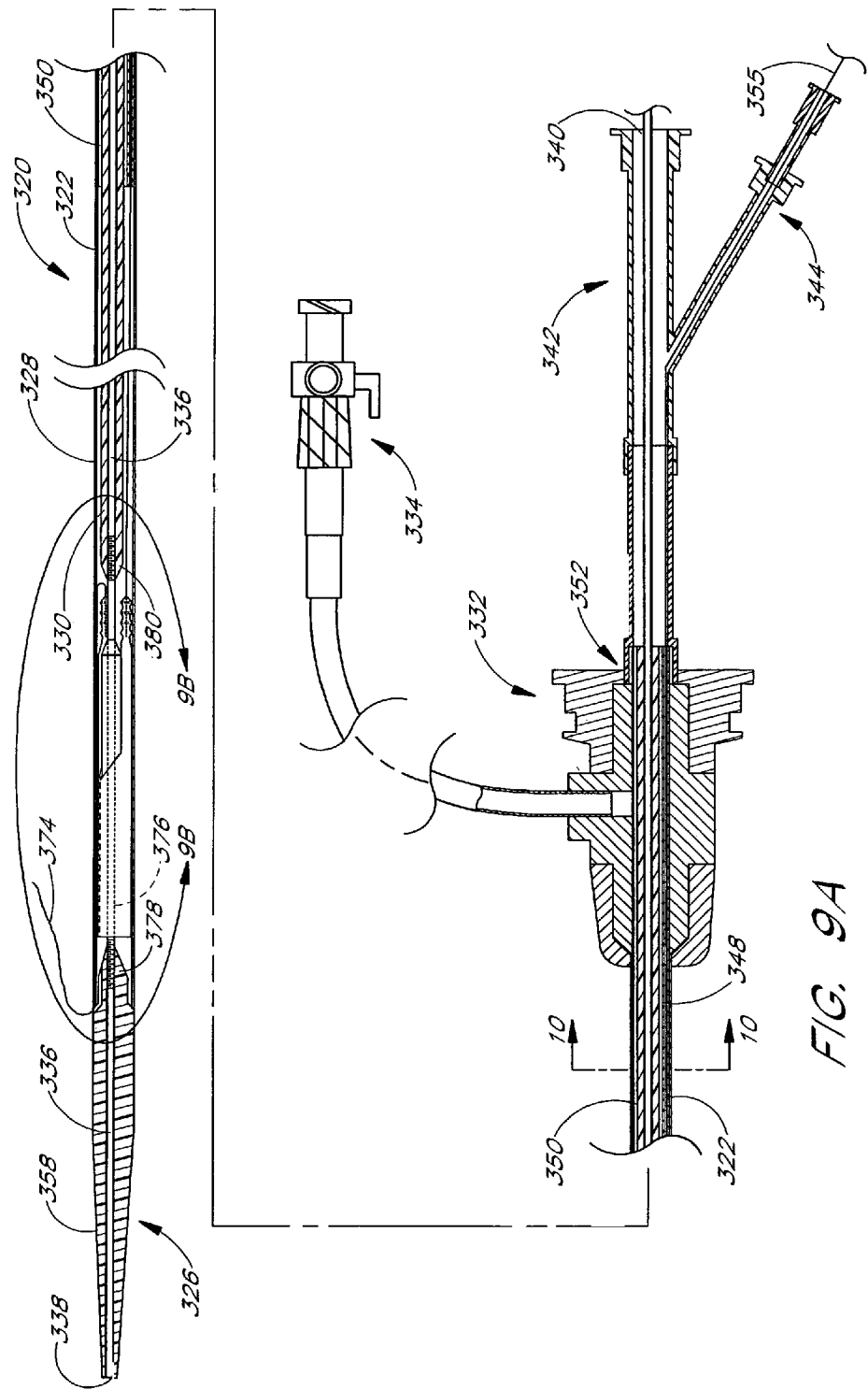
FIG. 9A is side elevational cross-section of a bifurcation graft delivery catheter in accordance with the present invention.

A deployment catheter 320 for deploying a self expandable bifurcation graft such as the one described above and having certain features and aspects according to the present invention will now be described with initial reference to FIGS. 9A-9C.

The deployment catheter 320 comprises an elongate flexible multicomponent tubular body 322 having a proximal end 324 and a distal end 326. The tubular body 322 and other components of this catheter 320 can be manufactured in accordance with any of a variety of techniques well known in the catheter manufacturing field. Suitable materials and dimensions can be readily selected taking into account the natural anatomical dimensions in the iliacs and aorta, together with the dimensions dictated by the desired percutaneous access site.

The elongate flexible tubular body 322 comprises an outer sheath 328, which is axially movably positioned upon a central tubular core 330. In one embodiment, the outer sheath 328 comprises extruded PTFE and/or PEEK, having an outside diameter of about 0.280" and an inside diameter of about 0.250". The outer sheath 328 preferably has an axial length within the range of from about 40" to about 55", and, in one embodiment of the catheter 320 having an overall length of 110 cm, the axial length of the outer sheath 328 is about 52". Preferably, the outer sheath 328 is provided at its proximal end with a manifold 332, having a hemostatic valve 334 thereon and access ports such as for the infusion of drugs or contrast media as will be understood by those of skill in the art.

The central core 330 defines, in part, a central guidewire lumen 336, which may in an over the wire construction extend throughout the length of catheter 320. The central lumen 336 has a distal exit port 338 and a proximal access port 340 as will be understood by those of skill in the art. As best seen in FIG. 9A, in the illustrated embodiment, the proximal access port 340 is defined by a backend connector 342, which is attached to the proximal end of the central core 330. The illustrated backend connector 342 preferably also defines a release wire port 344, the utility of which will be described below.

In a preferred embodiment, the central core 330 is axially movably positioned within but rotationally locked to the outer sheath 328. As such, the rotational orientation of the central core 330 remains fixed with respect to the rotational orientation of the outer sheath 328. Rotational engagement can be accomplished in any of a variety of ways, normally involving complementary surface structures such as keys or splines on the associated components. For example, the central core 330 can be provided with one or two or more radially outwardly extending projections, along a portion or all of its axial length. This projection is slidably received within a radially outwardly extending slot on the interior surface of the outer sheath 328, or a component secured thereto. Alternatively, a radially inwardly extending projection on the outer sheath 328 or an associated component can be received with an axially extending recess on the outer surface of the central core 330. Alternatively, any of a variety of non-round configurations for the central core 330 such as elliptical, oval, triangular, square, polygonal, and the like, can be slidably received within a complementary-shaped aperture on or connected to the outer sheath 328.

Figure 10:
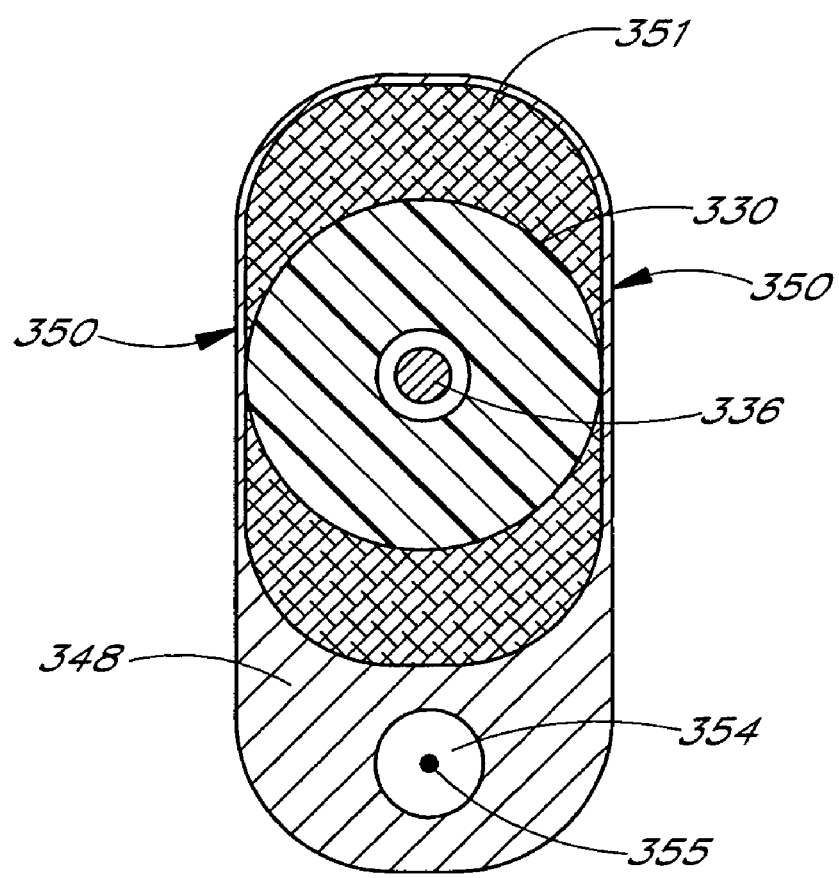
FIG. 10 is a cross-section taken along the line 10-10 in FIG. 9A.

In the illustrated embodiment, the central core 330 is provided with a proximal stiffening element 348 (see also FIG. 10), which may be in the form of a stainless steel hypotube with a non-round cross-section with two opposing flat sides 350 extending axially along its length. See FIG. 10. The illustrated stiffening element 348 is coupled to the central core 330 by an adhesive, such as, for example, an epoxy 351. A corresponding aperture is provided in a rotational lock 352 provided on the manifold 332. The resulting assembly enables rotation of the manifold 334 to cause a commensurate rotation of the central core 330. Specific dimensions and design details of the rotational lock 352 disclosed herein will be readily apparent to those of skill in the art in view of the disclosure herein. As shown in FIG. 10, the proximal stiffening element 348 preferably also defines a release wire lumen 354 for guiding a release wire 355 to the release wire port 344.

A distal segment of the deployment catheter 320 comprises an elongate flexible tapered distal tip 358. With particular reference to FIGS. 11A-C, the illustrated distal tip 358 includes a tapered portion 360, a first cylindrical portion 362 and a recessed portion 364. In one embodiment of the deployment catheter 320, the distal tip 358 has an axial length of approximately 73 millimeters. In such an embodiment, the tapered portion 360 has an axial length of approximately 48 millimeters, the first cylindrical portion 362 has an axial length of approximately 15 millimeters and the recessed portion 364 has an axial length of approximately 10 millimeters. However, it should be appreciated the length of the distal tip 358 and the length of the portions 360, 362, 364 can be varied depending upon the desired trackability and flexibility characteristics.

Preferably, the first cylindrical portion 362 has an outside diameter that is approximately equal to the outside diameter of the outer sheath 328. The tapered portion 360, in turn, preferably tapers from an outside diameter that is approximately equal to the outside diameter of the first cylindrical portion 362 to an outside diameter that is at least about 50% smaller at the distal end thereof.

In a preferred embodiment, the recessed portion 364 is configured to fit within the distal end of the outer sheath 328. In the illustrated embodiment, the recessed portion 364 preferably defines an annular shoulder 366, which prevents distal movement of the outer sheath 328 with respect to the distal tip 358. The illustrated recessed portion 364 also includes a second cylindrical portion 368 and a tapered proximal portion 370. The second cylindrical portion 368 is configured to fit within the distal end of the outer sheath 328 when the catheter 320 is in a loaded configuration. See FIG. 9B. Preferably, the second cylindrical portion 368 has an outer diameter that is slightly smaller than the inner diameter of the distal end of the outer sheath 328. The tapered portion 370 has a outer diameter that tapers in the proximal direction and terminates at the central lumen 336, which extends through the distal tip 358 from the proximal end to the distal end.

The distal tip preferably also includes a groove 372, which in the illustrated embodiment extends axially along the second cylindrical portion 368, through the annual shoulder 366 and the proximal end of the first cylindrical portion 362. As best seen in FIG. 9B, in a loaded configuration, the groove 372 provides a path for a contralateral guidewire 374, the utility of which will be described below.

Figure 12:
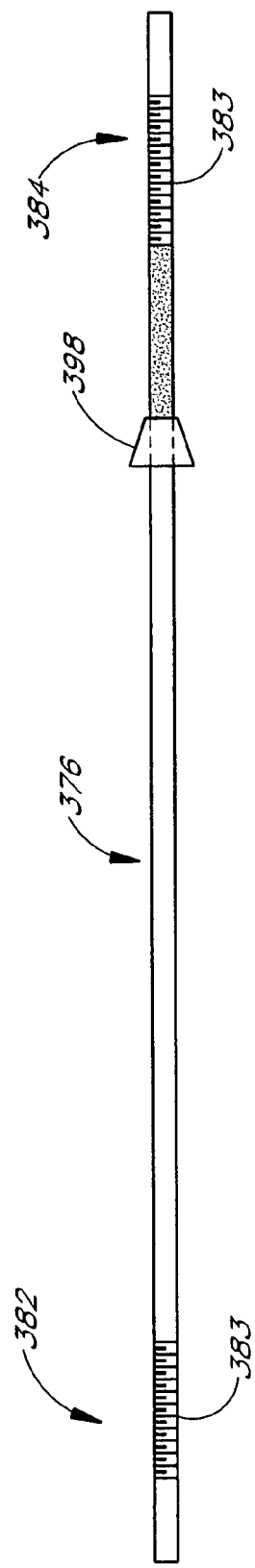
FIG. 12 is a side elevational view of a distal hypotube of the bifurcated delivery catheter shown in FIG. 9A.

The distal tip 358 is preferably coupled to the central core 330. In the illustrated embodiment, the distal tip 358 is coupled to the central core 30 through a distal hypotube 376, which is best seen in FIG. 12. The distal hypotube 376 may comprise a solid wall such as stainless steel, or a more flexible wall such as a braided polymide tubing. Preferably, the polyimide tubing has an inside diameter of about 0.059" and an outside diameter that is slight smaller than the diameter of the central lumen 336 at a proximal end 378 of the distal tip 358 and a distal end 380 of the central core 330. See FIG. 9B. An internal braid is may be made from 0.0015" stainless steel 304 wire at a pic count of about 50 braids per inch, such as may be obtained from Phelps Dodge (GA) or H.V. Technologies (GA). The use of flexible tubing such as spiral cut layers or woven or braided tubing in place of conventional stainless steel or other metal hypotubing increases the lateral flexibility of the assembled device, which facilitates the placement and deployment steps.

In the embodiment illustrated in FIG. 12, a distal end 382 of the hyptotube 376 is frictionally fitted within the proximal end 378 of the distal tip 358. To aid the frictional fit, the distal end 382 may be provided with a one or more ridges or grooves 383. In a similar manner, a proximal end 384 of the distal hypotube 376 is frictionally fitted within the distal end 380 of the central core 330. The proximal end 384 of the distal hypotube 376 may also be provided with one or more ridges or grooves 383. In other embodiments, the distal hypotube 376 can be connected to distal tip 358 and/or the central core 330 by thermal bonding, adhesive bonding, and/or any of a variety of other securing techniques known in the art which can also be used in addition to the frictional fit described above.

Figure 9B:
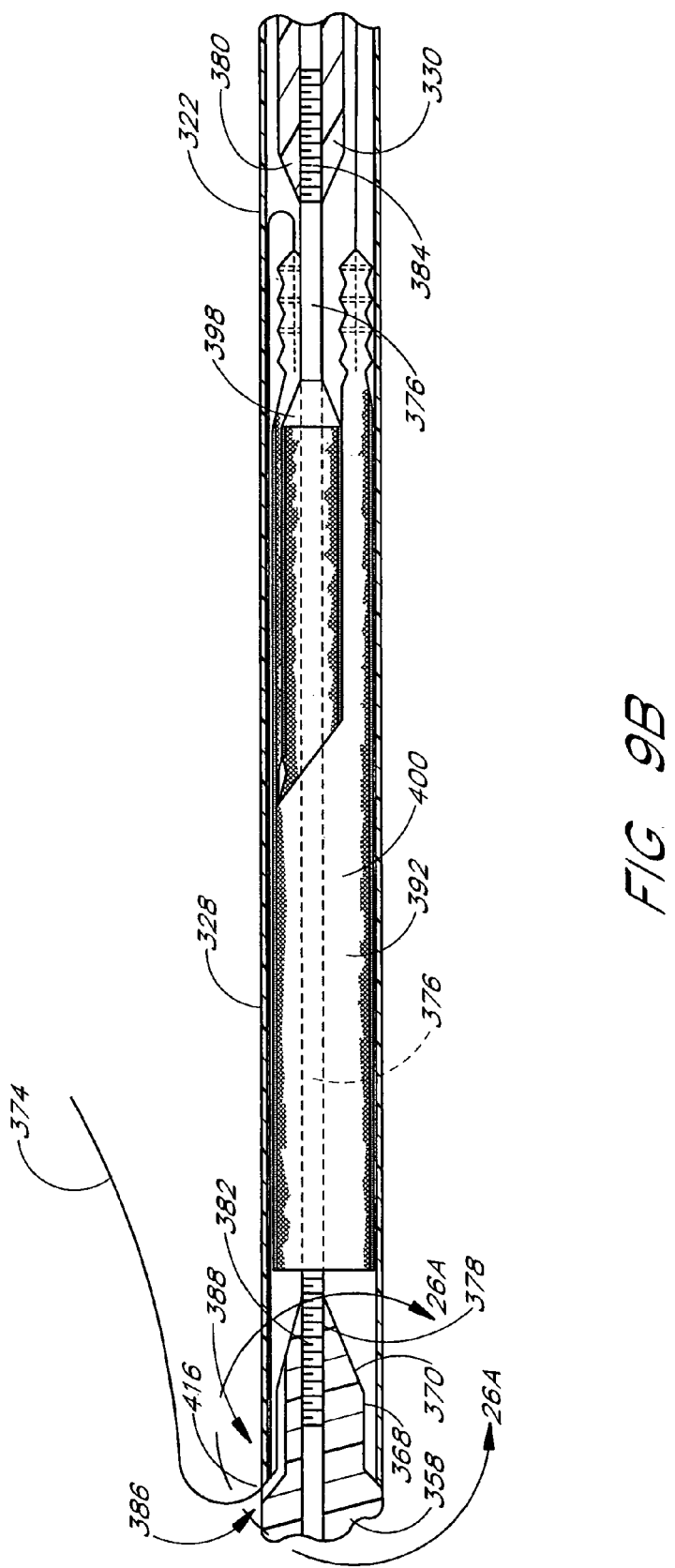
FIG. 9B is a closer view of a portion of FIG. 9A.

As can be seen from FIG. 9B, in a loaded configuration, a junction 386 is formed between a distal end 388 of the outer sheath 328 and the distal tip 358. As can be seen in FIG. 9C, proximal retraction of the outer sheath 328 with respect to the central core 330 will expose a bifurcated endoluminal graft 390, as will be discussed in more detail below.

Figure 9C:
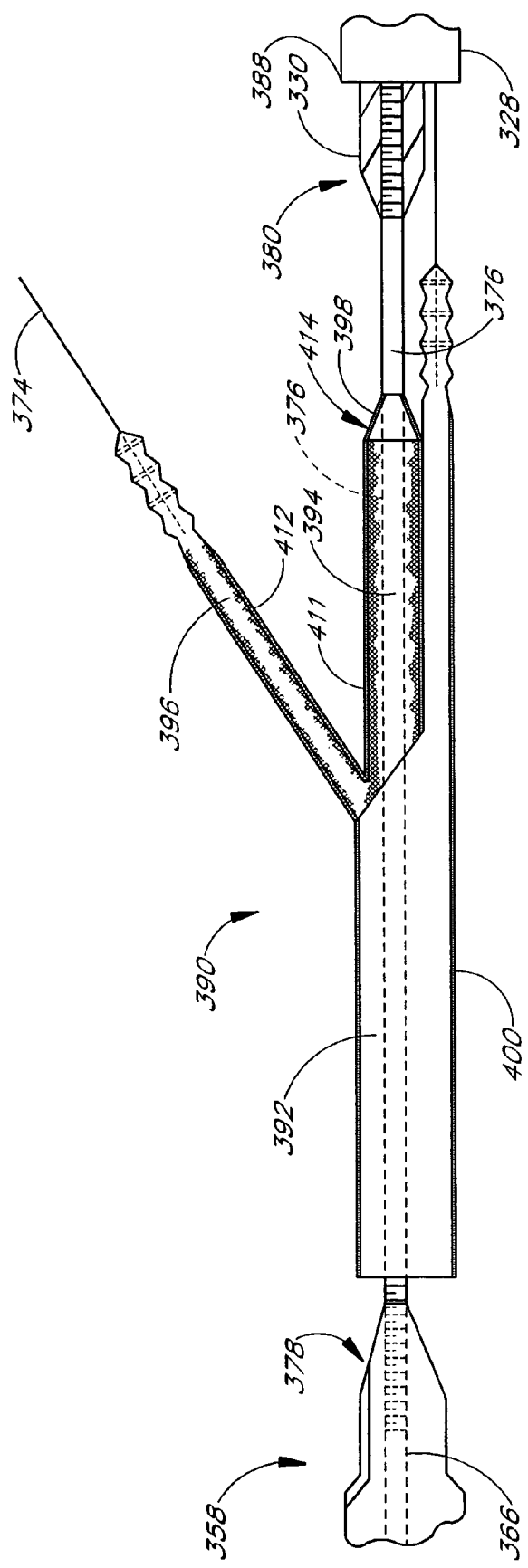
FIG. 9C is similar to the view shown in FIG. 9B with the bifurcation graft delivery catheter shown in a stent exposed configuration.

With continued reference to FIG. 9C, the bifurcated endoluminal graft 390 is illustrated in an exposed configuration. The graft 390 comprises aortic trunk portion 392, a proximal ipsilateral iliac branch 394, and a proximal contralateral iliac branch 396. In the loaded configuration (see FIG. 9B), the graft 390 is contained within the outer tubular sheath 328 between the proximal end of the distal tip 358 and the distal end 380 of the central core 330. Proximal movement of the graft 390 is prevented by a proximal stop 398, which is axially immovably connected to the distal hypotube 376. See also FIG. 12. The function of the proximal stop 398 can be accomplished through any of a variety of structures as will be apparent to those of skill in the art in view of the disclosure herein.

Figure 13:
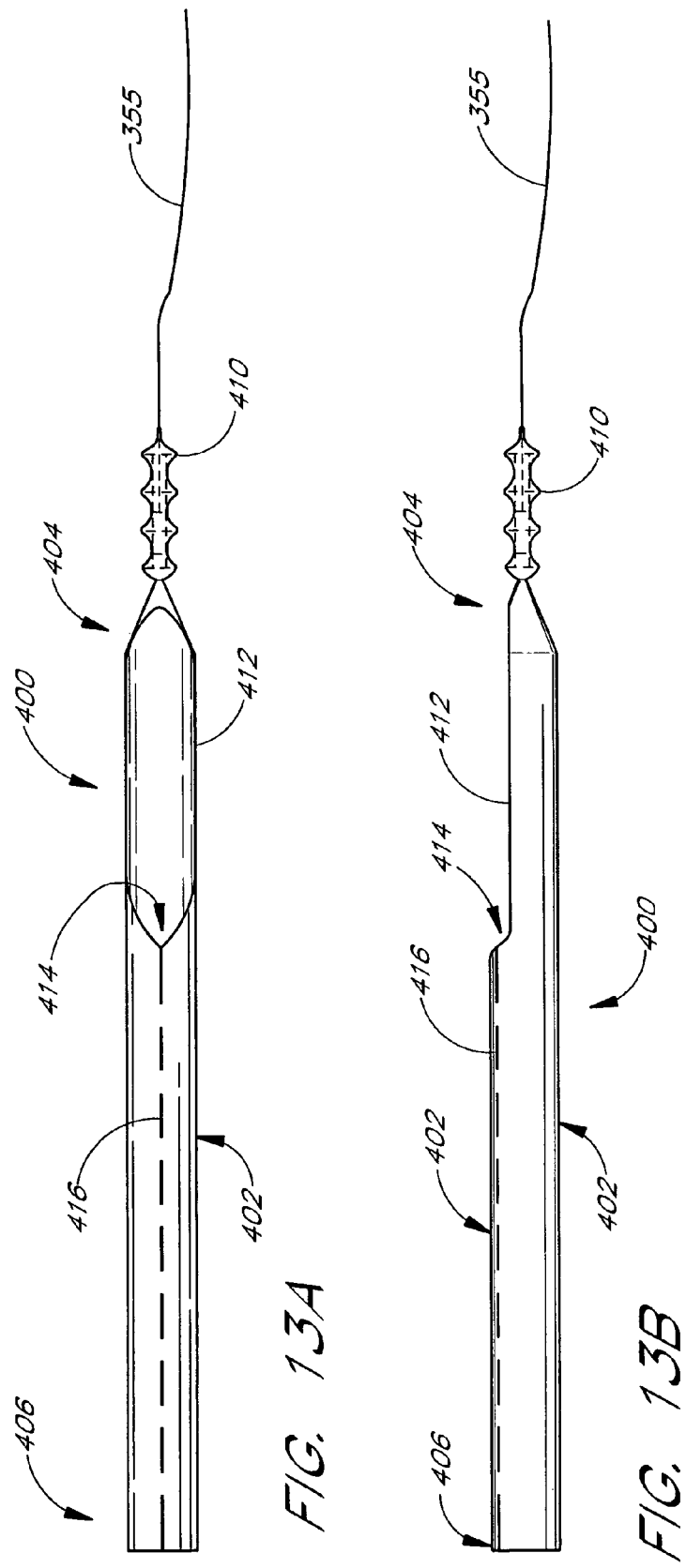
FIGS. 13A and B are top and side views of a peelable cover for restraining a portion of the bifurcated graft.

As mentioned above, proximal retraction of the outer sheath 328 will uncover the aortic trunk portion 392 and release the contralateral branch 396. In one embodiment, the aortic trunk portion 392 remains compressed within a peelable sheath 400. Referring to FIGS. 13A and 13B, the peelable sheath 400 comprises a tubular body 402 having a proximal end 404 and a distal end 406. The peelable sheath 400 is secured to the aortic trunk release wire 355. The aortic trunk release wire 355, in the illustrated embodiment, is secured by way of a joint 410 to the proximal end 404 of the peelable sheath 400. As shown in FIG. 9A, the release wire 355 extends through the catheter 320 between the outer sheath 328 and the inner core 330 and the release wire port lumen 354 exiting the catheter 320 at the release wire port 344.

Preferably, the proximal end 404 of the peelable sheath 100 is provided with a leader 412 of sheath material to facilitate positioning the joint 410, as will be explained below. The peelable sheath 400 is preferably also provided with a peel start point 414 such as a slit, perforation, V-shaped cut, or otherwise as will be apparent to those of skill in the art in view of the disclosure herein. The peelable sheath 400 preferably further includes a perforation line 416, crease, recess or other tear facilitating modification extending axially there along to facilitate predictable tearing of the material. In the illustrated embodiment, the perforation line 416 comprises a series of slits that are about 2.0 millimeters long and separated by a distance of about 1.5 millimeters.

The peelable sheath 400 may be made from any of a variety of thin, tearable materials as will be apparent to those of skill in the art in view of the disclosure herein. Preferably, the material exhibits sufficient strength that it will restrain the self expandable aortic trunk portion 392 while at the same time maintaining a low cross sectional profile and also permitting tearing to occur with a minimal amount of traction required on the release wire 355. In one embodiment, the peelable sheath 400 comprises a PTFE tube having a wall thickness of about 0.012", an outside diameter of about 0.218" and a length from the peel start point 414 to the distal end 406 of about 10.0 cm. The overall length from the joint 410 to the distal end 406 is about 17.0 cm. Of course, specific dimensions may be optimized for any particular device as will be understood in the art. Other thin wall tearable materials may also be used, such as PET, HDPE, or PE.

Referring to FIG. 9C, the iliac branches 394 and 396 will also remain compressed within a first (ipsilateral) tubular sheath 411 and a second (contralateral) tubular sheath 412. The first tubular sheath 411 is configured to restrain the ipsilateral branch 394 of the graft 390 in the constrained configuration. The first tubular sheath 411 is adapted to be axially proximally removed from the ipsilateral branch 394, thereby permitting the branch to expand to its implanted configuration. In one embodiment, the first tubular sheath 411 comprises a thin walled PTFE extrusion having an outside diameter of about 0.215" and an axial length of about 7.5 cm. A proximal end 414 of the tubular sheath 411 is necked down such as by heat shrinking to secure the first tubular sheath 411 to the distal hypotube 376. In this manner, proximal withdrawal of the distal hypotube 376 will proximally advance the first tubular sheath 411 relative to the graft 390, thereby deploying the self expandable ipsilateral branch 394 of the graft 390.

The second tubular sheath 412 is secured to the contralateral guidewire 374, which extends outside the catheter 320 at a point 416 (see FIG. 9B), such as may be conveniently provided at the junction 386 between the outer tubular sheath 328 and the distal tip 358. In the illustrated embodiment, the contralateral guidewire 374 extends through the groove 372 provided in the distal tip 358 and described above. The second tubular sheath 412 is adapted to restrain the contralateral branch 396 of the graft 390 in the reduced profile. In one embodiment of the invention, the second tubular sheath 412 has an outside diameter of about 0.215" and an axial length of about 7.5 cm. In the loaded configuration (FIG. 9B), the second tubular sheath 412 can have a significantly smaller cross-section than the first tubular sheath 411, due to the presence of the hypotube 376 within the ipsilateral branch 394.

As mentioned above, the second tubular sheath 412 is secured at its proximal end to the contralateral guidewire 374. This may be accomplished through any of a variety of securing techniques, such as heat shrinking, adhesives, mechanical interfit and the like. In one embodiment, the contralateral guidewire 374 is provided with one or more knots or other diameter enlarging structures to provide an interference fit with the proximal end of the second tubular sheath 412, and the proximal end of the second tubular sheath 412 is heat shrunk and/or bonded in the area of the knot to provide a secure connection. The same attachment structure can be used for the peelable sheath 400 as well. Any of a variety of other techniques for providing a secure connection betweeen the corresponding wire and the tubular sheath can readily be used in the context of the present invention as will be apparent to those of skill in the art in view of the disclosure herein. The contralateral guidewire 374 and release wire 355 can comprise any of a variety of structures, including polymeric monofilament materials, braided or woven materials, metal ribbon or wire, or conventional guidewires as are well known in the art.

Figure 14:
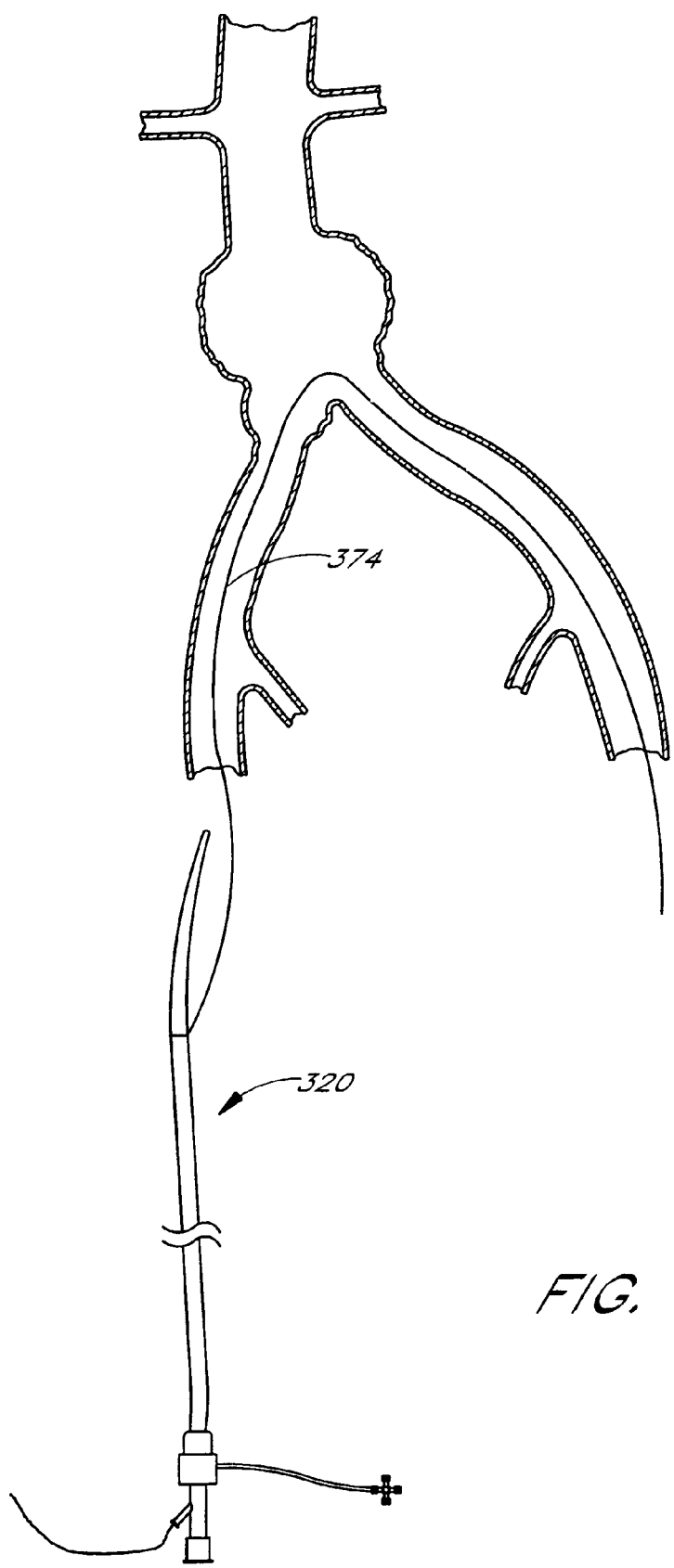
FIG. 14 is a schematic representation of a bifurcated graft deployment catheter of the present invention before being inserted into the ipsilateral iliac and the aorta, with the contralateral guidewire positioned within the contralateral iliac

Referring to FIG. 14, in use, the free end of the contralateral guidewire 374 is percutaneously inserted into the arterial system, such as at a first puncture in a femoral artery. The contralateral guidewire 374 is advanced through the corresponding iliac towards the aorta, and crossed over into the contralateral iliac in accordance with cross over techniques, which are well known in the art. The contralateral guidewire 374 is then advanced distally down the contralateral iliac where it exits the body at a second percutaneous puncture site.

Figure 15:
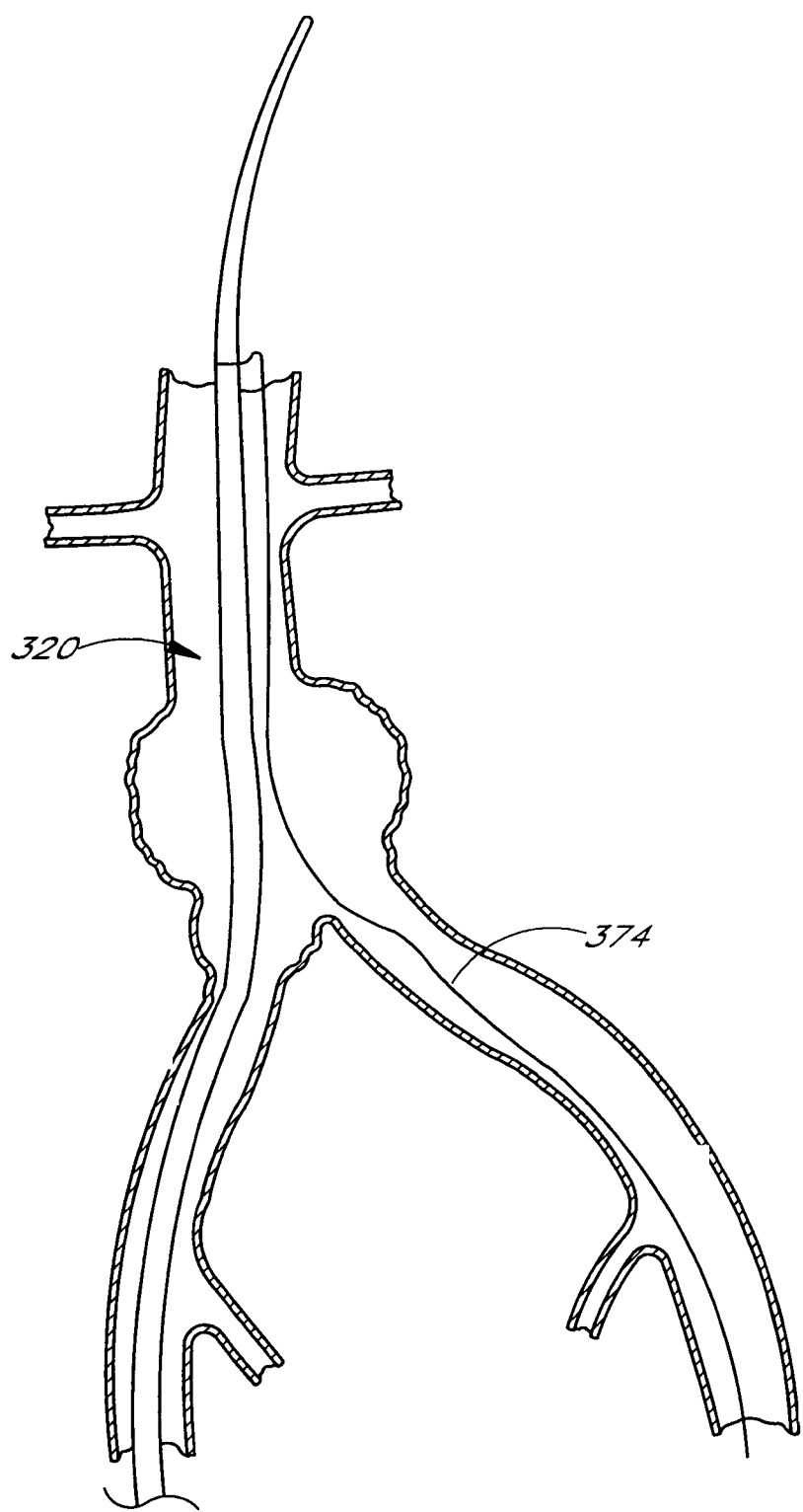
FIG. 15 is a schematic representation of a bifurcated graft deployment catheter of the present invention, positioned within the ipsilateral iliac and the aorta, with the contralateral guidewire positioned within the contralateral iliac.
Figure 16:
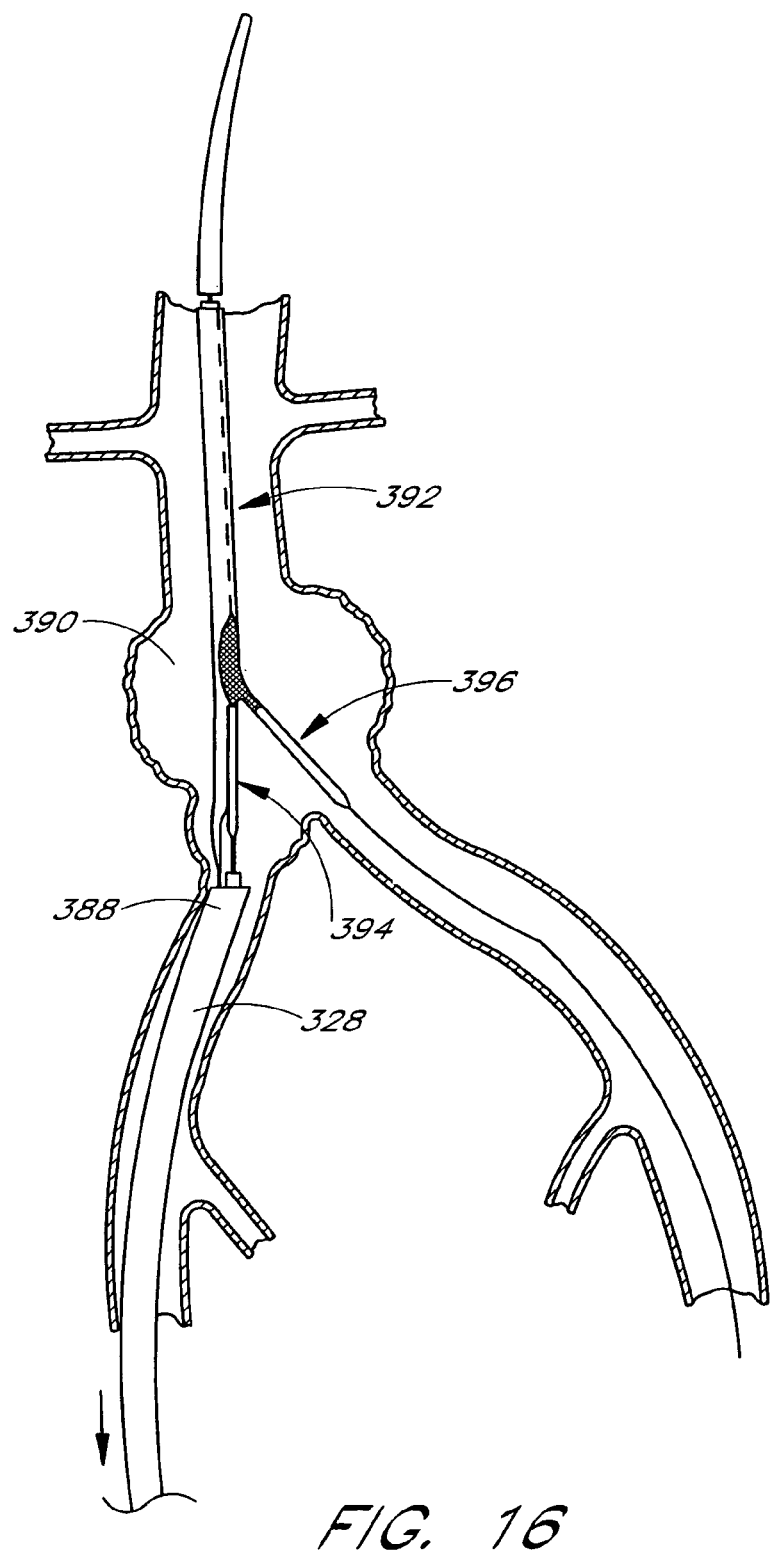
FIG. 16 is a schematic representation as in FIG. 15, with the outer sheath proximally retracted and the compressed iliac branches of the graft moving into position within the iliac arteries.

The catheter 320 is thereafter percutaneously inserted into the first puncture, and advanced along a guidewire (e.g. 0.035 inch) through the ipsilateral iliac and into the aorta. As the deployment catheter 320 is transluminally advanced, slack produced in the contralateral guidewire 374 is taken up by proximally withdrawing the contralateral guidewire 374 from the second percutaneous access site. In this manner, the catheter 320 is positioned in the manner generally illustrated in FIG. 15. Referring to FIG. 16, the outer sheath 328 is proximally withdrawn while generally maintaining the axial position of the overall deployment catheter 320, thereby exposing the aortic trunk 392 and releasing the first and second iliac branches 394, 396 of the graft 390.

Figure 17:
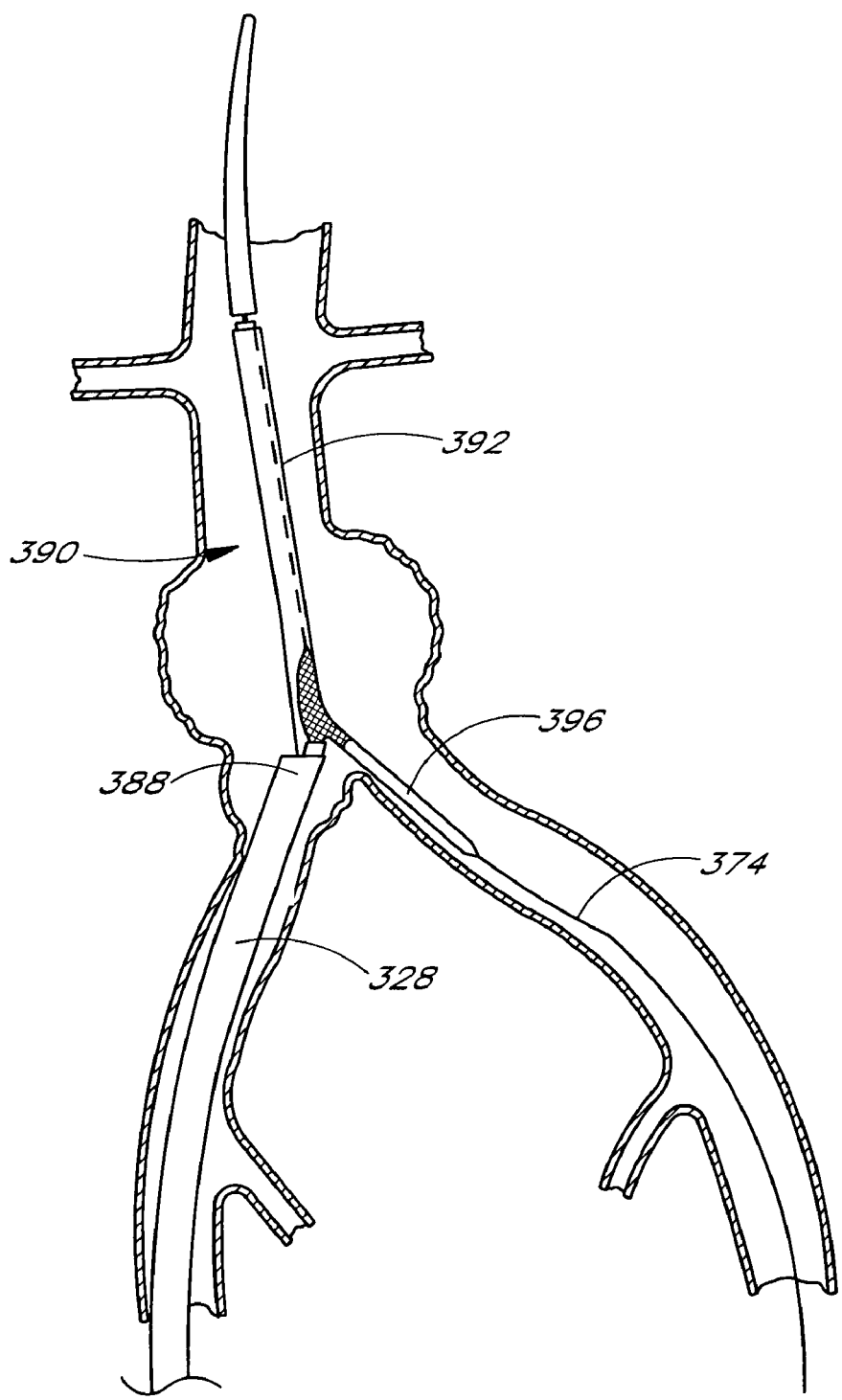
FIG. 17 is a schematic representation as in FIG. 16, with the outer sheath distally moved as compared to FIG. 16 so as to support the graft within the bifurcation.
Figure 18:
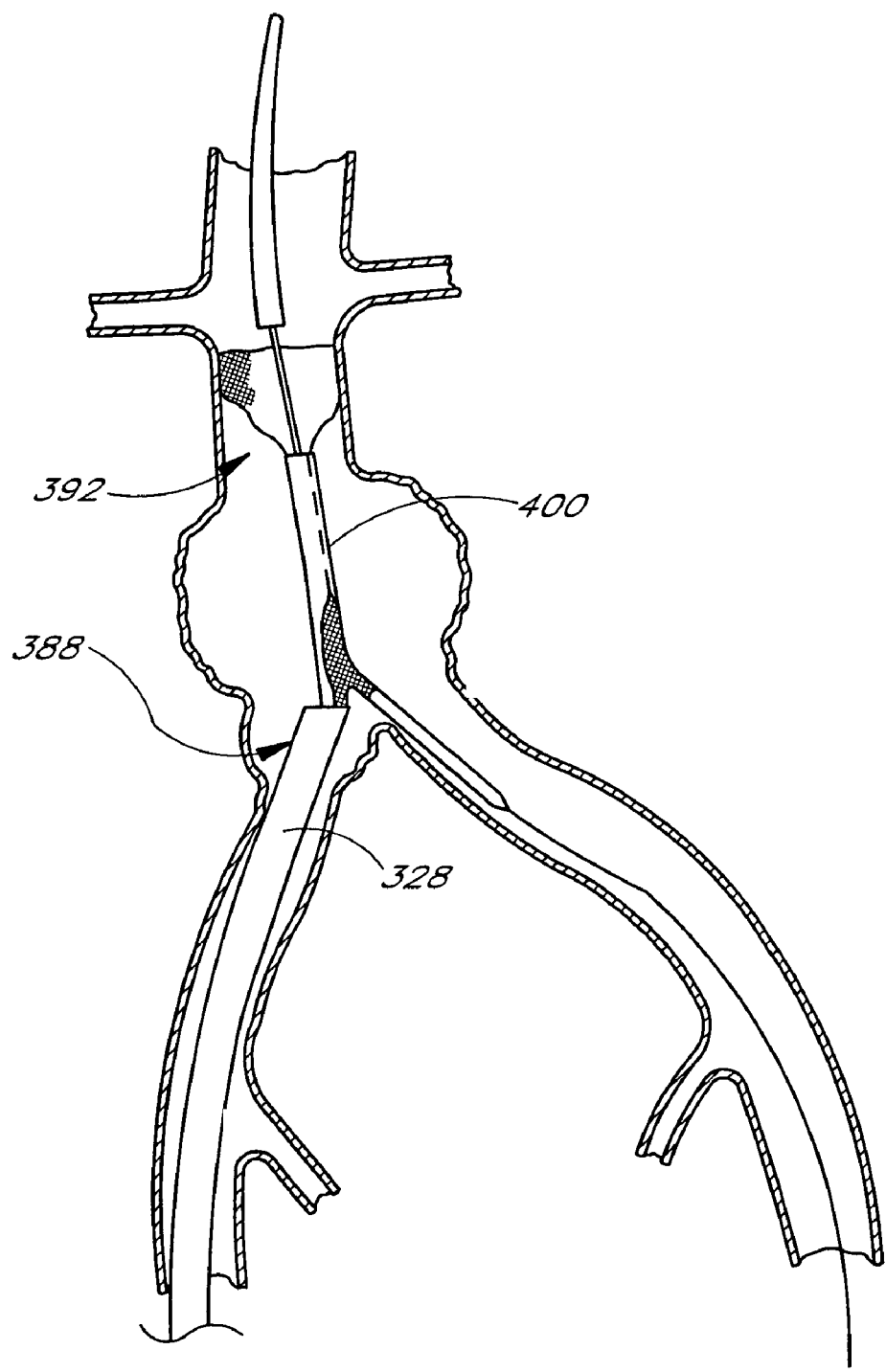
FIG. 18 is a schematic representation as in FIG. 17, with the main aortic trunk of the graft partially deployed within the aorta.
Figure 19:
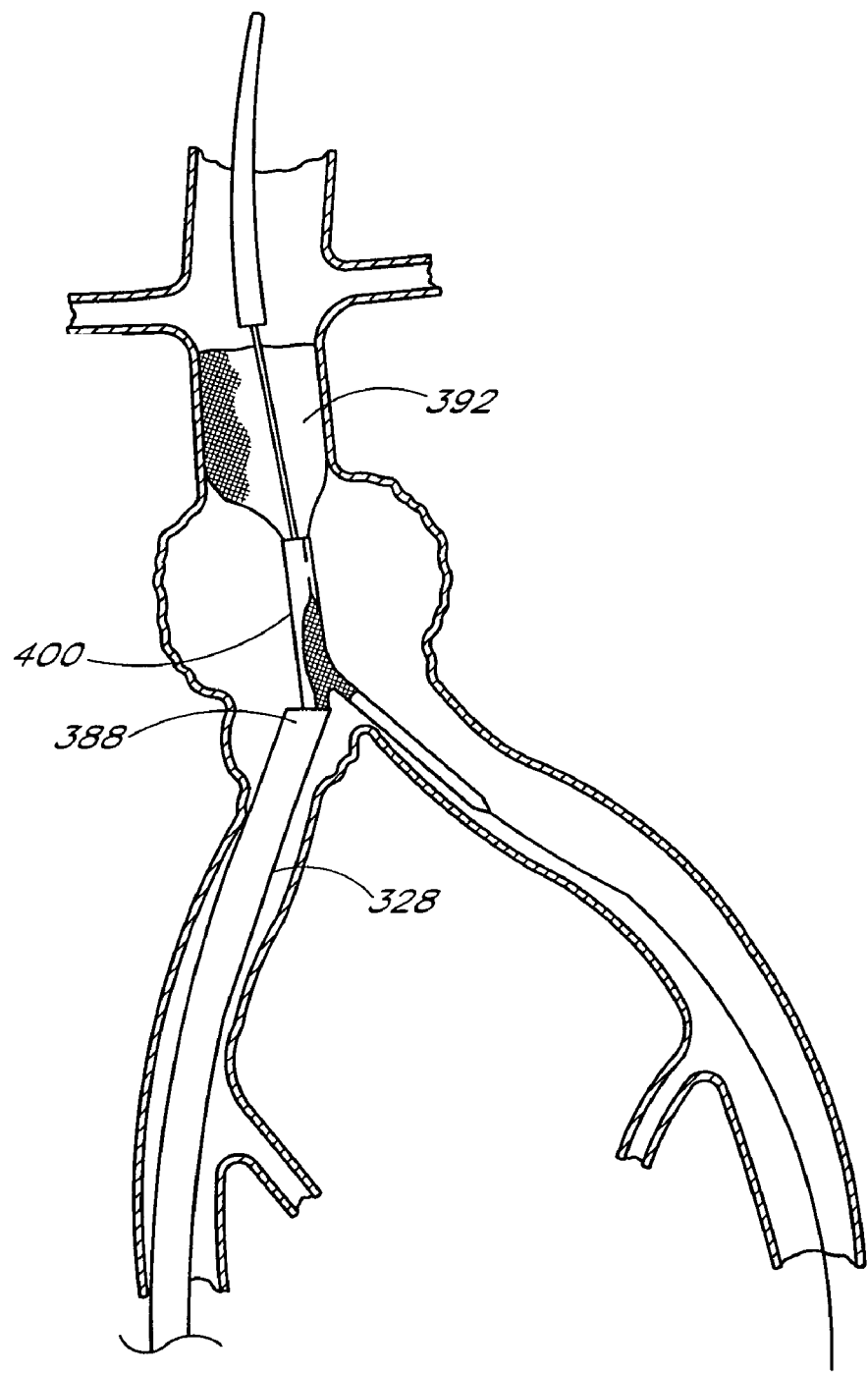
FIG. 19 is a schematic representation as in FIG. 18, with the main aortic trunk of the graft more fully deployed within the aorta.
Figure 20:
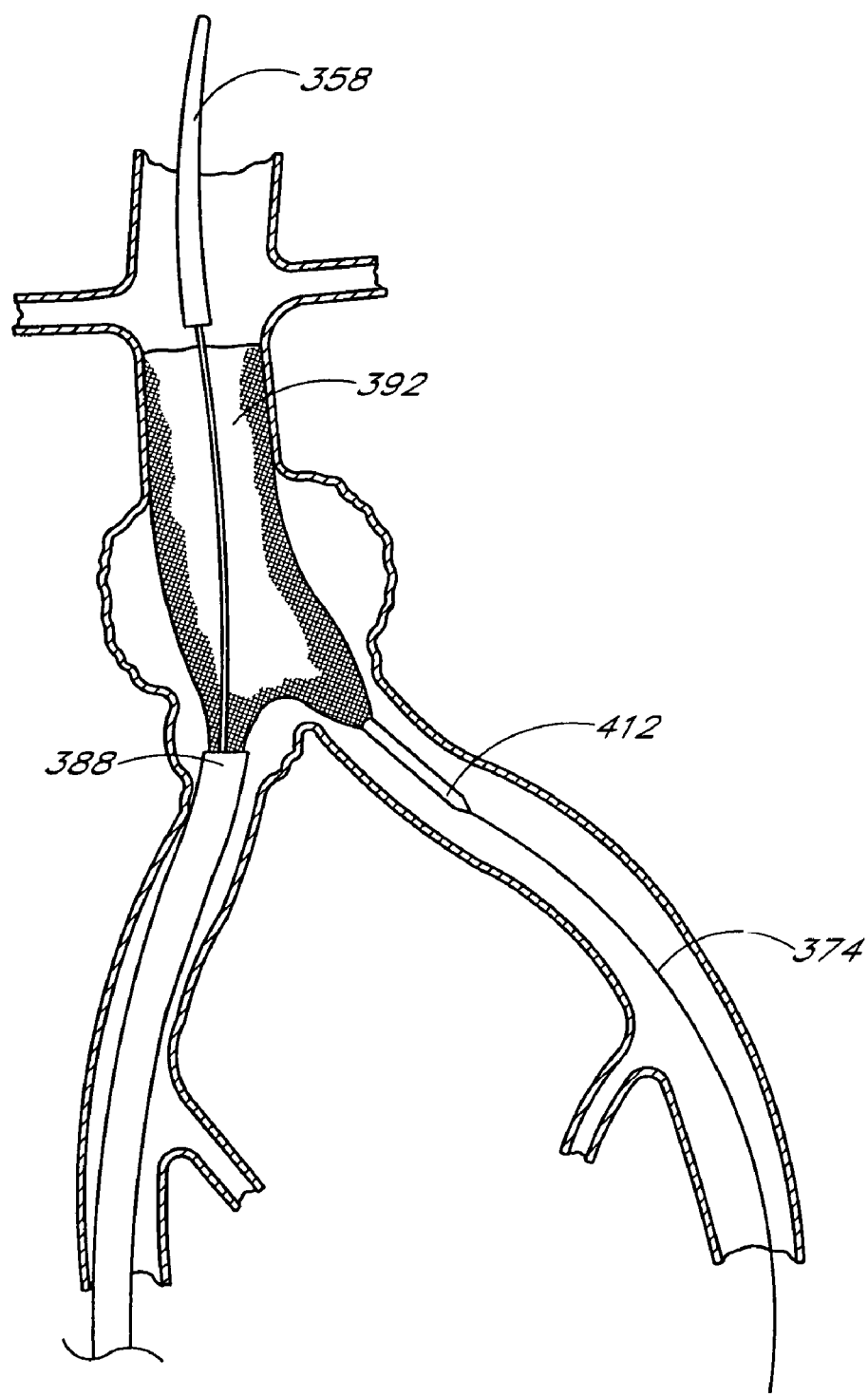
FIG. 20 is a schematic representation as in FIG. 19, with the main aortic trunk of the graft fully deployed within the aorta.

Referring to FIG. 17, the outer sheath 328 can be distally advanced and contralateral guidewire 374 withdraw so as to position the iliac position the branches 394, 396 of the graft 390 within the iliac arteries as illustrated. In this embodiment, the outer sheath 328 also provides support for the ispsilateral branch 394. Referring to FIG. 18, proximal traction is applied to the aortic trunk release wire 355. In the illustrated embodiment, the distal end 388 of the outer sheath 328 provides a fulcrum for minimizing injury to the adjacent tissue as proximal traction is applied to the aortic trunk release wire 355. Proximal retraction of the release wire 355 pulls the peelable sheath 400 down into the outer sheath 328. As shown in FIG. 19, retraction of the release wire 355 pulls the peelable sheath 400 proximally along the aortic trunk 392 such that the aortic trunk 392 is released from the distal end first. Further proximal retraction of the release wire 410 causes the peelable sheath 400 to tear or split distally thereby permitting complete retraction of the peelable sheath 400 from the aortic trunk 392 as illustrated in FIG. 20.

Following deployment of the aortic trunk 392, the contralateral guidewire 374 is thereafter proximally withdrawn, thereby by proximally withdrawing the second sheath 412 from the contralateral iliac branch 396 of the graft 390. See FIG. 21. The contralateral branch 396 of the graft 390 thereafter self expands to fit within the contralateral iliac artery. The guidewire 374 and sheath 412 may thereafter be proximally withdrawn and removed from the patient, by way of the second percutaneous access site.

Figure 21:
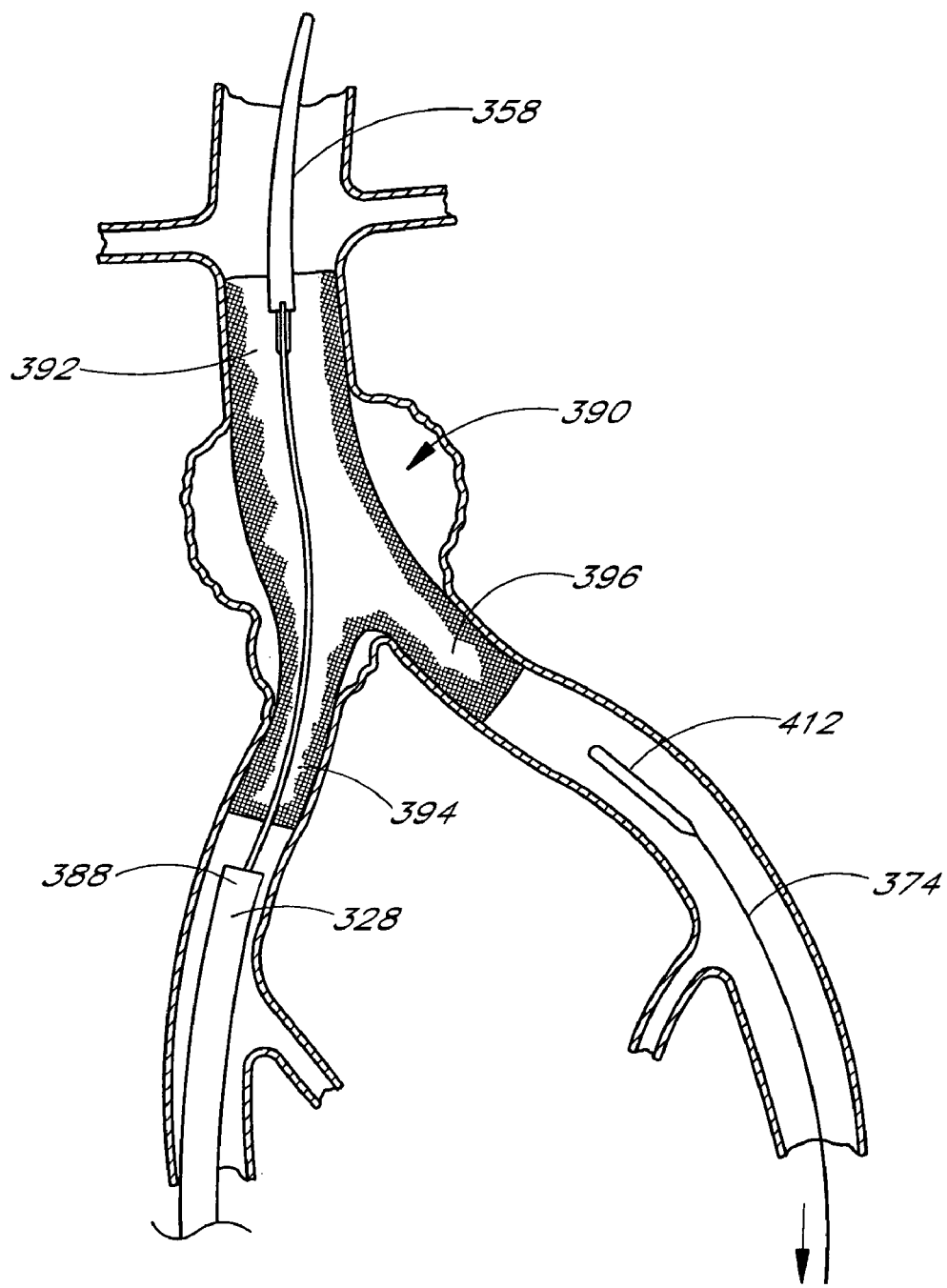
FIG. 21 is a schematic representation as in FIG. 20, with both of the contralateral and ipsilateral iliac branches of the graft deployed.
Figure 22:
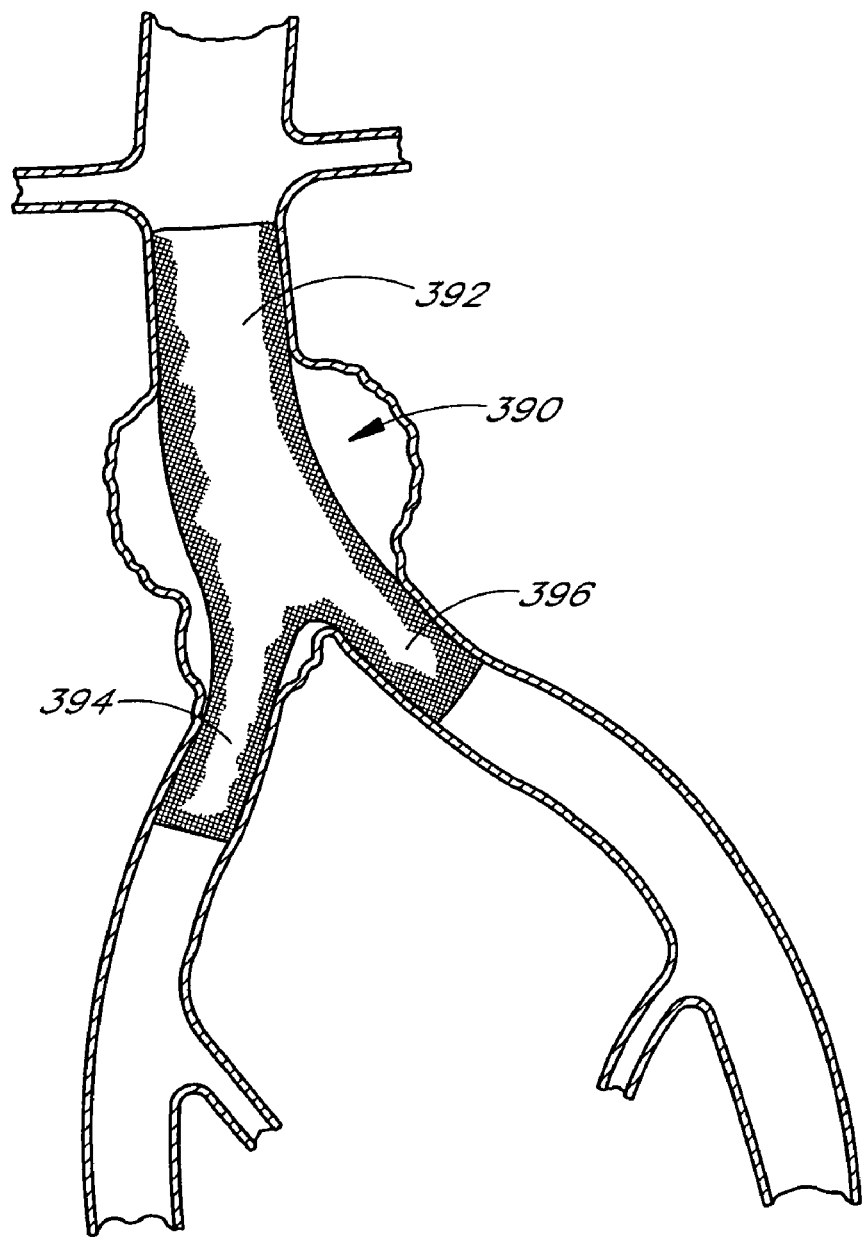
FIG. 22 is a schematic representation as in FIG. 21, following removal of the deployment catheter.

Thereafter, the outer sheath 328 may be proximally withdrawn to expose the ipsilateral branch 394 of the graft 390. As shown in FIG. 21, following deployment of the ipsilateral branch 386 of the graft 390, a central lumen through the aortic trunk 392 is sufficiently large to permit proximal retraction of the distal tip 358 through the deployed graft 390. As such, the inner core 330 may be proximally withdrawn to release the ipsilateral branch 394 from the first tubular sheath 411. Following deployment of the ipsilateral branch 394, the central lumen through the aortic trunk 392 and ipsilateral branch 394 is sufficiently large to permit complete proximal retraction of the deployment catheter 320 through the graft 390. As shown in FIG. 22, the graft 390 is now fully deployed and the deployment catheter 230 may thereafter be proximally withdrawn from the patient by way of the first percutaneous access site.

Figure 23:
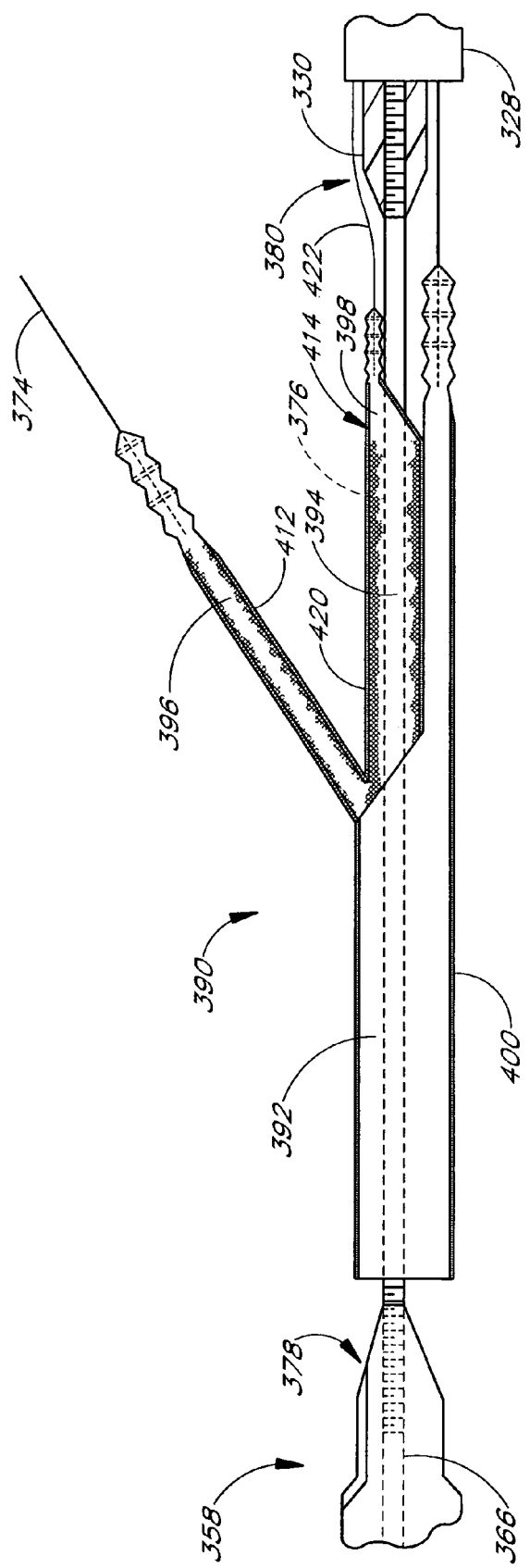
FIG. 23 is a cross-sectional side view of a modified embodiment of a bifurcation graft delivery system with the bifurcation graft delivery catheter shown in a stent exposed configuration.

Another technique, which has certain features and advantages according to the present invention, for deploying a self expandable bifurcation graft will now be described with reference to FIG. 23.

In this embodiment, the ipsilateral branch 394 is compressed within a second peelable sheath 420, which preferably is configured in a manner similar to the peelable sheath 410 described above. The second peelable sheath 420 is secured to an ipsilateral branch release wire 422, which as with the aortic trunk release wire 410 can extend proximally through the catheter 320 between the outer sheath 328 and the inner core 330. The ipsilateral branch release wire 422 can exit the catheter 320 through the release wire port 344 (see FIG. 9A). Of course, in a modified embodiment, a second release port can be provided.

In one embodiment, the ipsilateral branch 394 is released by proximally withdrawing the ipsilateral branch release wire 422 after the aortic trunk 392 and the contralateral branch 396 of the graft 390 have been released as described above. In such an arrangement, the second peelable sheath 420 is preferably not secured to the inner core 330. As such, releasing the ipsilateral branch 394 does not require proximal movement of the inner core 330. In one embodiment, the distal end 374 of the outer sheath 328 can be used to provide a fulcrum for minimizing injury to the adjacent tissue as proximal traction is applied to the release wire 422.

Figure 24:
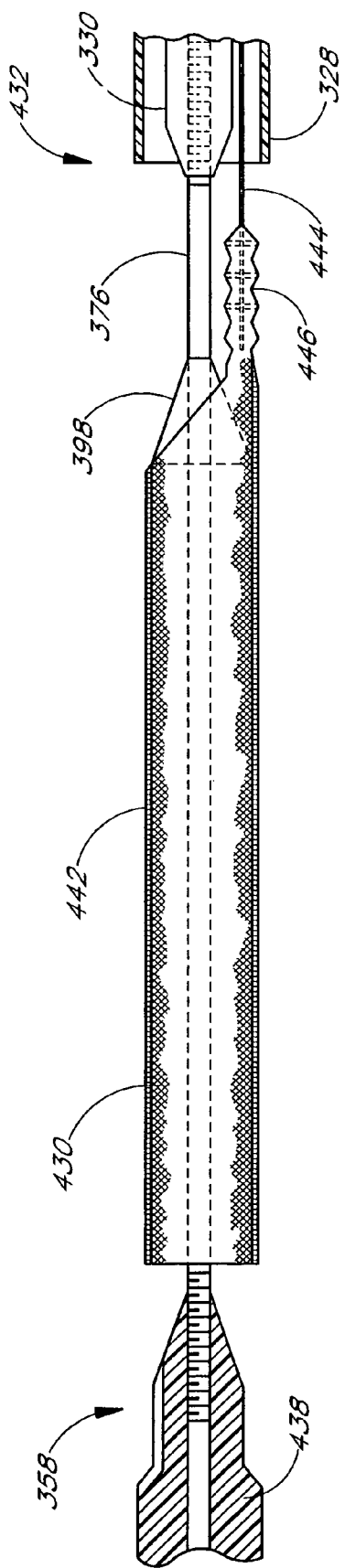
FIG. 24 is a cross-sectional view of a portion of a straight tube graft delivery system.

Certain aspects of the techniques describe above can also be used to deploy a self expandable straight tube graft. Such a straight tube graft is described in U.S. Pat. No. 6,197,049, the contents of which are hereby incorporated by reference herein. Such a technique, which has certain features and advantages according to the present invention, for deploying a self expandable straight tube graft 430 will now be described with reference to FIGS. 24 and 25.

In the illustrated embodiment, a deployment catheter 432 is configured in a manner substantially similar to the catheter 320 described above. As such, like numbers are used to refer to parts similar to those of FIGS. 9A-C. The illustrated catheter 432 includes an outer sheath 328, inner core 330 and a distal tip 358. The inner core 330 is connected to a distal tip 358 through a hypotube 376, which includes a proximal stop 398 for preventing proximal movement of the graft 430 on the hypotube 376. The graft 430 is positioned on the hypotube 376. In the loaded configuration (not shown), the outer sheath 328 covers the graft 430.

The graft 430 is compressed within a peelable sheath 442, which preferably is configured in a manner similar to the peelable sheath 410 described above. The peelable sheath 442 is secured to a release wire 444 through a joint 446. The release wire 444 preferably extends through the catheter 432 between the outer sheath 328 and the inner core 330.

In use, the catheter 432 is percutanously inserted into a first puncture in the femoral artery and advanced along a guide wire through the ipsilateral iliac and into the aorta. Once the catheter 432 is in the proper position, the outer sheath 328 can proximally withdrawn while maintaining the general axial position of the catheter 432, thereby exposing the graft 430. The graft 430 is released by proximally withdrawing the release wire 444. After the graft 430 is released, the central lumen through the graft 430 is sufficiently large to permit complete proximal retraction of the distal tip 438. The catheter 432 may thereafter be proximally withdrawn from the patient by way of the first access site.

Figure 25:
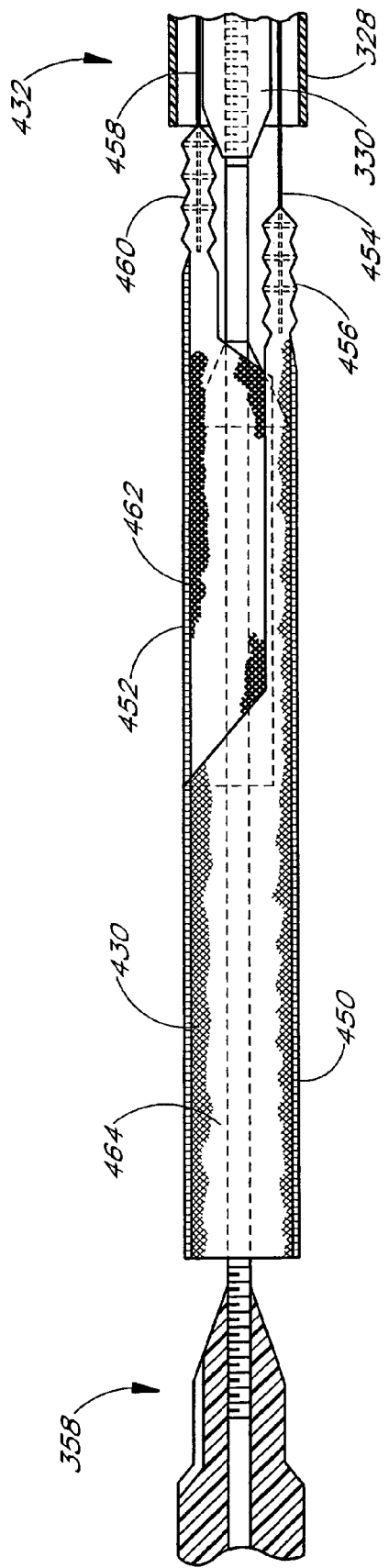
FIG. 25 is a cross-sectional view of a portion of a modified embodiment of a straight tube graft delivery system.

Referring to FIG. 25, another modified embodiment of a technique for deploying a self expandable straight tube graft 430 is illustrated. In this embodiment, the straight tube graft 430 is compressed with a distal peelable sheath 450 and a proximal peelable sheath 452, which are configured in a manner similar to the peelable sheaths described above. The distal peelable sheath 450 is attached to a distal release wire 454 through a junction 456 and in a similar manner the proximal peelable sheath 452 is attached to a proximal release wire 458 through a junction 460.

After the catheter 432 is in position, the outer sheath 328 is proximally withdrawn while maintaining the general axial position of the catheter 432, thereby exposing the graft 430. A device proximal (anatomically inferior) portion 462 of the graft 130 is then released by proximally withdrawing the proximal release wire 458. After the proximal portion 462 of the graft 430 is released, the distal portion 464 of the graft is released by proximally withdrawing the distal release wire 454. Preferably, the distal portion 464 is released after the proximal portion 462 so as to prevent a "sail" effect in the thoracic area due to the high pressure, although release can be accomplished in the reverse order.

Once the graft 430 has been deployed, the central lumen through the graft is sufficiently large to permit complete proximal retraction of the distal tip 358. The catheter 432 may thereafter be proximally withdrawn from the patient by way of the first access site. The forgoing two step deployment structure can also be utilized on the main aorta portion of a bifurcation graft, if deployment anatomically distal to proximal is preferred over the previously disclosed anatomically proximal to distal. See, e.g., FIGS. 17-19.

As the catheter 320, 432 is transluminally advanced along the guidewire through the ipsilateral iliac and into the aorta, it is advantgeous for the surgeon to be able to visualize the position of the distal end 388 of the outer sheath 328 so as to be able to more accurately place the graft within the patient. Catheters may be conventionally formed from extruded PTFE and/or PEEK, which are transparent under fluoroscopic visualization. To aid the visualization of the catheter, the distal end 388 of the outer sheath 329 preferably includes a band 500 of any of a variety of radio opaque ("RO") materials that are well known in the art as shown in FIGS. 26A and 26B. In the illustrated embodiment, the distal end 388 of the outer catethter 328 is provided with a groove 352, in which the band 500 is positioned. In a modified embodiment, the distal end 388 can be formed without the groove 352 and the band 500 can be bonded directly around the outer sheath 328.

Figure 29B:
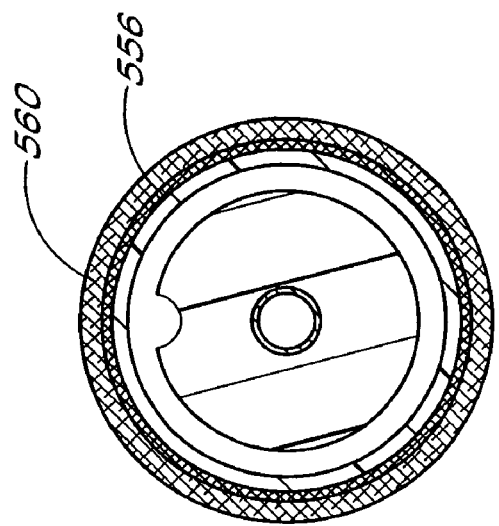
FIG. 29B is a cross-sectional view taken through line 29B-29B of FIG. 26A.
Figure 29A:
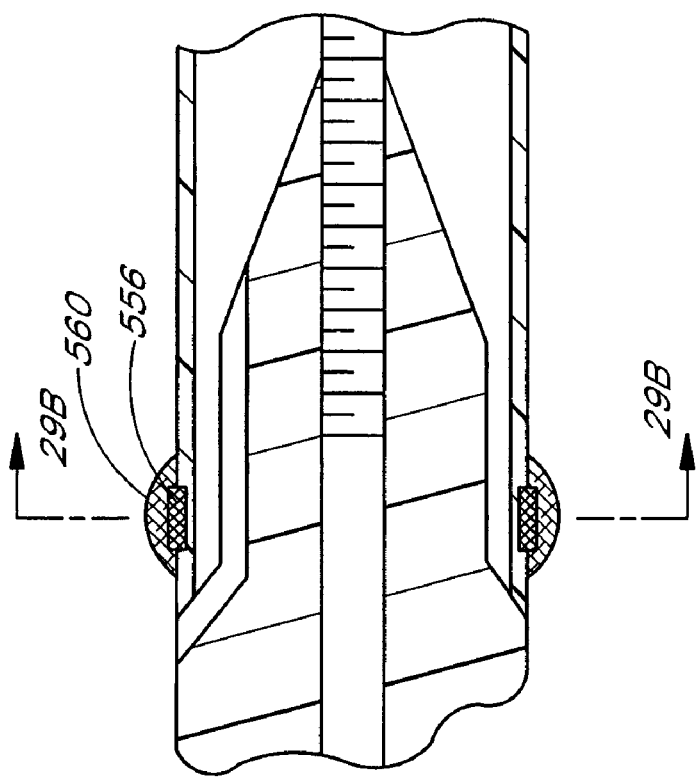
FIG. 29A is still another modified embodiment of the portion shown in FIG. 26A.

FIGS. 27A and 27B illustrate another embodiment for providing RO material on the catheter. In this embodiment, RO fixtures or staples 354 are inserted through the outer sheath 328 at the distal end 388. FIGS. 28A and 28B illustrate yet another embodiment for providing RO material on the catheter. In this embodiment, the distal end 388 of the outer sheath 328 includes a band 556 of RO material that is positioned on the sheath 328 or within a groove 558. The distal end 388 of the outer sheath 328 is inverted proximally over the band 556 so as to cover the outer surface of the band. The outer sheath 328 may then be thermally bonded or adhesively bonded to itself proximal the marker bands 556, to enclose the marker band 556. In the embodiment shown FIGS. 29A and 29B, the band 556 is covered by a layer 560 of shrink wrap tubing, epoxy or similar material. In other embodiments, RO material can be dispersed in the PEEK or PTFE material, which forms the body of the catheter. In such an embodiment, the density of the RO material is preferably higher at the distal end 388 of the outer sheath 328. In still other embodiments, the RO material can be attached to or dispersed within the distal tip 358 and/or the inner core 330 in a manner similar to that described above.

While a number of variations of the invention have been described in detail, other modifications and methods of use will be readily apparent to those of skill in the art. Accordingly, it should be understood that various applications, modifications and substitutions may be made of equivalents without departing from the spirit of the invention or the scope of the claims.

What is claimed is:

1. A bifurcation prosthesis deployment system, comprising:
    an elongate, flexible catheter body, having a proximal end and a distal end and comprising an outer sheath and an inner core that is axially moveable with respect to the outer sheath and an atraumatic distal tip coupled to the inner core and positioned adjacent the distal end of the catheter body;
    a self-expanding bifurcated graft comprising a main vessel portion, a first branch vessel portion, and a second branch vessel portion;
    a main vessel graft restraint comprising a first peelable cover for restraining substantially the entire length of the main vessel portion of the bifurcated graft;
    a first branch vessel graft restraint, for restraining the first branch vessel portion of the graft; and
    a second branch vessel graft restraint, for restraining the second branch vessel portion of the graft;
    wherein:
        the first peelable cover is coupled to a main branch release element;
        each of the bifurcated graft, main vessel graft restraint, first branch vessel graft restraint, and the second branch vessel graft restraint are positioned within the catheter body in a graft loaded condition in an orientation such that the main vessel portion is positioned nearer to the distal end of the catheter body than either the first branch vessel portion or the second branch vessel portion; and
        the first peelable cover is configured such that proximal retraction of the first peelable cover causes the first peelable cover to tear.

2. A deployment system as in claim 1, wherein the main branch release element comprises an elongate, flexible, axially moveable release element extending through the catheter.

3. A deployment system as in claim 1, wherein the first branch vessel graft restraint comprises a first tubular sleeve.

4. A deployment system as in claim 3, wherein the first tubular sleeve is coupled to the inner core.

5. A deployment system as in claim 1, wherein the first branch vessel graft restraint comprises a second peelable cover.

6. A deployment system as in claim 5, wherein the second peelable cover is attached to a first branch release element comprising an elongate, flexible, axially moveable release element also extending through the catheter.

7. A deployment system as in claim 1, wherein the second branch vessel graft restraint comprises a tubular sleeve.

8. A deployment system as in claim 7, wherein the tubular sleeve is attached to a second branch release element comprising an elongate, flexible, axially moveable release element.

9. A deployment system as in claim 8, wherein the catheter is configured to enter through a first percutaneous puncture site and the second branch release element is configured to exit through a second percutaneous puncture site.

10. The deployment system of claim 1, comprising a self-expanding wire support for deployment within the bifurcated graft, the wire support comprising a main component, a first branch component, and a second branch component, wherein:
    the wire support is self-expandable along substantially the entire length thereof;
    the main component of the wire support is configured to support substantially the entire length of the main vessel portion of the graft;
    the first branch component of the wire support is configured to support substantially the entire length of the first branch vessel portion of the graft; and
    the second branch component of the wire support is configured to support substantially the entire length of the first branch vessel portion of the graft.

11. The deployment system of claim 1, wherein the main branch release element extends proximally and is configured to withdraw the first peelable cover by proximal retraction of the main branch release element.

12. The deployment system of claim 1, wherein the main branch release element is connected to a proximal end portion of the first peelable cover and does not extend distally past the proximal end portion of the first peelable cover.

13. The deployment system of claim 1, wherein the first branch vessel graft restraint restrains substantially the entire length of the first branch vessel portion of the graft, and the second branch vessel graft restrains substantially the entire length of the second branch vessel portion of the graft.

14. The deployment system of claim 1, wherein the first peelable cover comprises a peel start point.

15. The deployment system of claim 14, wherein the first peelable cover comprises at least one of a slit, a perforation, and a v-shaped cut.

16. The deployment system of claim 1, wherein the first peelable cover comprises at least one of a perforation line, a slit, a crease, and a recess extending axially along at least a portion thereof to facilitate tearing of the first peelable cover.

17. A deployment system for deploying a bifurcated prosthesis at the junction of a main vessel and first and second branch vessels, comprising:
 a delivery catheter having an inner core, an outer sheath and a distal tip that is coupled to the inner core, the inner core being slidably engaged within the outer sheath; and
 a self-expanding bifurcated prosthesis having a main body section with proximal and distal ends and being self-expandable along a substantial portion of the length thereof, and first and second branch sections at the proximal end of the main body section, each being self-expandable along a substantial portion of the length thereof;
 wherein:
  at least a portion of the main body section is held in a radially compressed state by a first peelable cover, the first branch section is held in a radially compressed state within a first tubular cover, and the second branch section is held in a radially compressed state within a second tubular cover;
  the main body section is deployable by proximally retracting the first peelable cover;
  the first peelable cover is configured such that proximal retraction of the first peelable cover causes the first peelable cover to tear; and
  the compressed bifurcated prosthesis is positioned within the outer sheath such that the distal end of the bifurcated prosthesis is positioned nearer to the distal tip of the delivery catheter.

18. The deployment system of claim 17, wherein the bifurcated prosthesis further comprises an expansion spring having an apex and first and second leg portions, wherein the leg portions are connected to respective first and second branch sections.

19. The deployment system of claim 17, wherein the first tubular cover is a peelable cover.

20. The deployment system of claim 17, wherein a distal end of the outer sheath includes an RO marker.

21. The deployment system of claim 20, wherein the RO marker comprises a band of RO material.

22. The deployment system of claim 17, further including means for marking a distal end of the outer sheath with RO material.

23. A bifurcation prosthesis deployment system, comprising:
 an elongate, flexible catheter body, having a proximal end and a distal end and comprising an outer sheath and an inner core that is axially moveable with respect to the outer sheath and an atraumatic distal tip coupled to the inner core and positioned adjacent the distal end of the catheter body;
 a self-expanding bifurcated graft comprising a main vessel portion, a first branch vessel portion, and a second branch vessel portion;
 a main vessel graft restraint comprising a first peelable cover for restraining substantially the entire length of the main vessel portion of the bifurcated graft;
 a first branch vessel graft restraint, for restraining the first branch vessel portion of the graft; and
 a second branch vessel graft restraint, for restraining the second branch vessel portion of the graft;
 wherein:
  the first peelable cover is coupled to a main branch release element;
  each of the bifurcated graft, main vessel graft restraint, first branch vessel graft restraint, and the second branch vessel graft restraint are positioned within the catheter body in a graft loaded condition in an orientation such that the main vessel portion is positioned nearer to the distal end of the catheter body than either the first branch vessel portion or the second branch vessel portion; and
  the deployment system is configured such that proximal retraction of the main branch release element in an axial direction causes the first peelable cover to tear.

24. A deployment system as in claim 23, wherein the main branch release element comprises an elongate, flexible, axially moveable release element extending through the catheter.

25. A deployment system as in claim 23, wherein the first branch vessel graft restraint comprises a first tubular sleeve.

26. A deployment system as in claim 25, wherein the first tubular sleeve is coupled to the inner core.

27. A deployment system as in claim 23, wherein the first branch vessel graft restraint comprises a second peelable cover.

28. A deployment system as in claim 27, wherein the second peelable cover is attached to a first branch release element comprising an elongate, flexible, axially moveable release element also extending through the catheter.

29. A deployment system as in claim 23, wherein the second branch vessel graft restraint comprises a tubular sleeve.

30. A deployment system as in claim 29, wherein the tubular sleeve is attached to a second branch release element comprising an elongate, flexible, axially moveable release element.

31. A deployment system as in claim 30, wherein the catheter is configured to enter through a first percutaneous puncture site and the second branch release element is configured to exit through a second percutaneous puncture site.

* * * * *

UNITED STATES PATENT AND TRADEMARK OFFICE
CERTIFICATE OF CORRECTION

| | | |
|---|---|---|
| PATENT NO. | : 8,034,100 B2 | Page 1 of 1 |
| APPLICATION NO. | : 10/722367 | |
| DATED | : October 11, 2011 | |
| INVENTOR(S) | : Samuel M. Shaolian et al. | |

It is certified that error appears in the above-identified patent and that said Letters Patent is hereby corrected as shown below:

Column 2, line 59, After "cover" delete "for".

Column 4, line 33, After "iliac" insert --.--.

Column 5, line 10, After "26A" insert --.--.

Column 5, line 37, Change "prosthesis," to --prosthesis.--.

Column 6, line 32, Change "and or" to --and/or--.

Column 8, line 39, Change "slideable" to --slidable--.

Column 10, line 27, Change "min" to --mm--.

Column 12, line 29, Change "polymide" to --polyamide--.

Column 14, line 32, Change "betweeen" to --between--.

Column 14, line 67, Change "ispsilateral" to --ipsilateral--.

Column 16, line 25, Change "percutanously" to --percutaneously--.

Column 17, line 3, Change "advantgeous" to --advantageous--.

Column 17, line 13, Change "catethter" to --catheter--.

Signed and Sealed this
Nineteenth Day of June, 2012

David J. Kappos
*Director of the United States Patent and Trademark Office*